(12) United States Patent
Osorio et al.

(10) Patent No.: US 12,414,742 B2
(45) Date of Patent: *Sep. 16, 2025

(54) APPARATUS AND SYSTEMS FOR EVENT DETECTION USING PROBABILISTIC MEASURES

(71) Applicant: Flint Hills Scientific, L.L.C., Lawrence, KS (US)

(72) Inventors: Ivan Osorio, Leawood, KS (US); Alexey Lyubushin, Moscow (RU); Didier Sornette, Zurich (CH)

(73) Assignee: Flint Hills Scientific, LLC, Lawrence, KS (US)

( * ) Notice: Subject to any disclaimer, the term of this patent is extended or adjusted under 35 U.S.C. 154(b) by 1308 days.

This patent is subject to a terminal disclaimer.

(21) Appl. No.: 16/808,814

(22) Filed: Mar. 4, 2020

(65) Prior Publication Data

US 2020/0253559 A1  Aug. 13, 2020

Related U.S. Application Data

(60) Division of application No. 13/598,339, filed on Aug. 29, 2012, now Pat. No. 10,595,787, which is a continuation-in-part of application No. 13/559,116, filed on Jul. 26, 2012, now Pat. No. 10,537,251, and a continuation-in-part of application No. 13/554,367, filed on Jul. 20, 2012, now Pat. No. 9,549,677, and a continuation-in-part of application No. 13/554,694, filed on Jul. 20, 2012, now Pat. No. 10,206,591.

(60) Provisional application No. 61/547,567, filed on Oct. 14, 2011.

(51) Int. Cl.
| | |
|---|---|
| *G16C 60/00* | (2019.01) |
| *A61B 5/00* | (2006.01) |
| *A61B 5/374* | (2021.01) |
| *G06F 30/10* | (2020.01) |
| *G06F 30/25* | (2020.01) |
| *G06F 113/26* | (2020.01) |
| *G16C 20/10* | (2019.01) |

(52) U.S. Cl.
CPC ............. *A61B 5/726* (2013.01); *A61B 5/374* (2021.01); *A61B 5/4094* (2013.01)

(58) Field of Classification Search
CPC ........ A61B 5/726; A61B 5/374; A61B 5/4094
See application file for complete search history.

(56) References Cited

U.S. PATENT DOCUMENTS

| 10,595,787 B2* | 3/2020 | Osorio | A61B 5/4094 |
| 2010/0121215 A1* | 5/2010 | Giftakis | A61N 1/36082 |
| | | | 600/595 |
| 2013/0030317 A1* | 1/2013 | Tanner | A61B 5/4094 |
| | | | 600/545 |

* cited by examiner

*Primary Examiner* — Olivia M. Wise
*Assistant Examiner* — Vy Rossi
(74) *Attorney, Agent, or Firm* — CF3; Stephen Eisenmann

(57) ABSTRACT

Methods, systems, and apparatus for determining probabilistic measures of seizure activity (PMSA) values based on a plurality of seizure detection algorithms and/or body signals used as inputs by the seizure detection algorithms. Use of the PMSA values to detect seizure activity based on a consensus of the algorithms and/or body signals, and/or warn, log, administer a therapy, or assess the efficacy of a therapy.

6 Claims, 17 Drawing Sheets

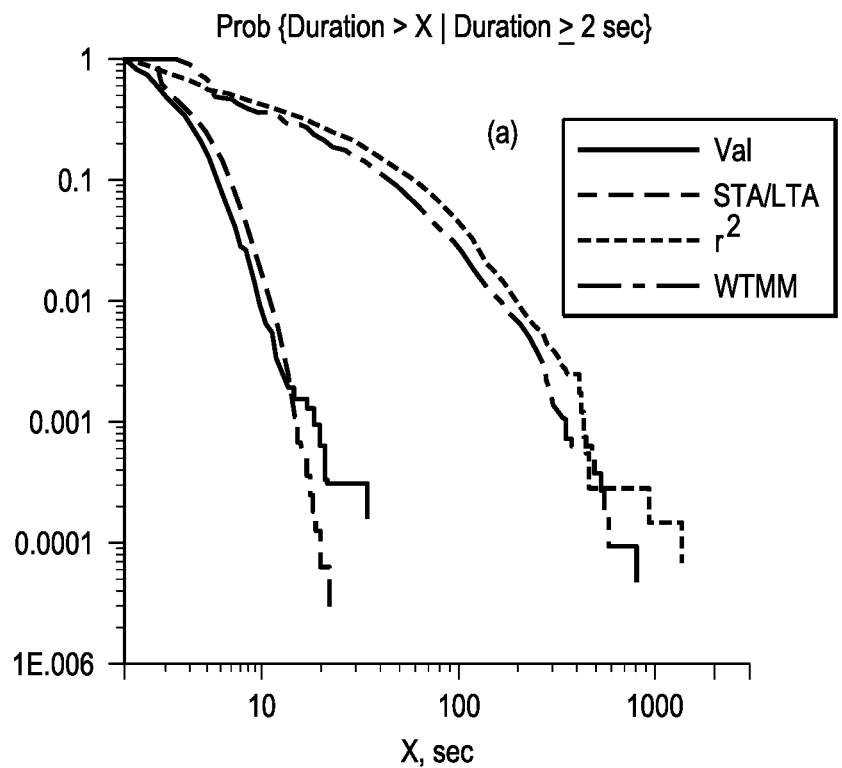
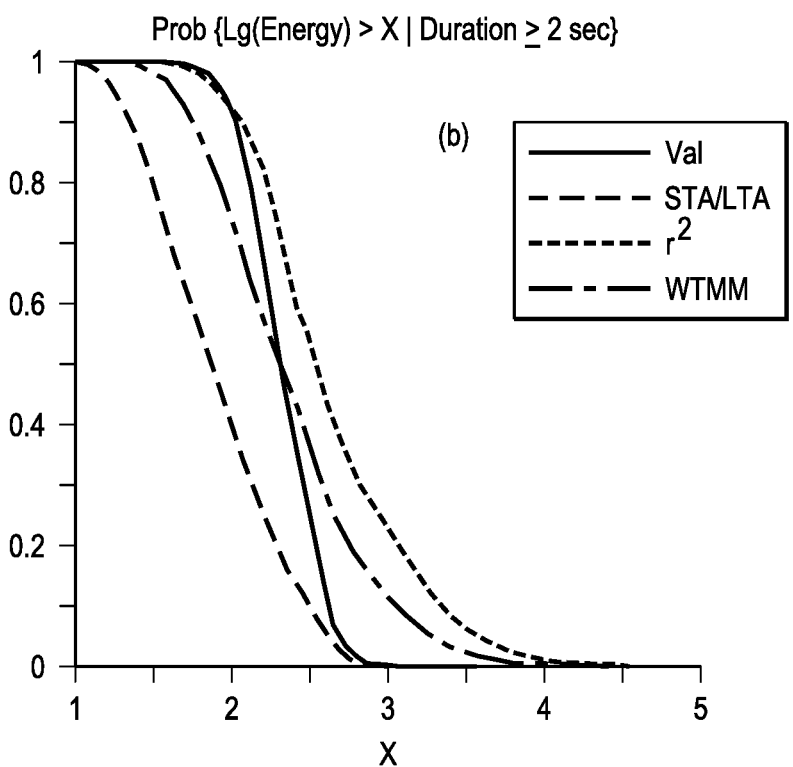
FIG. 12

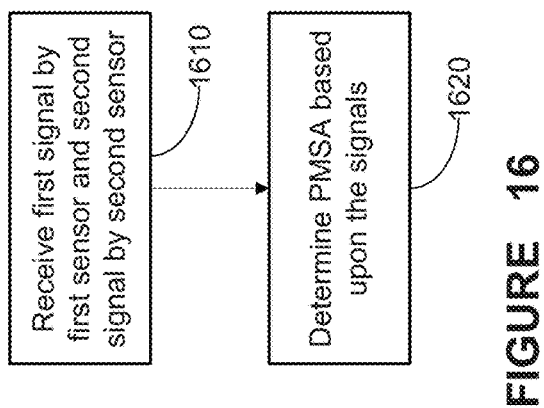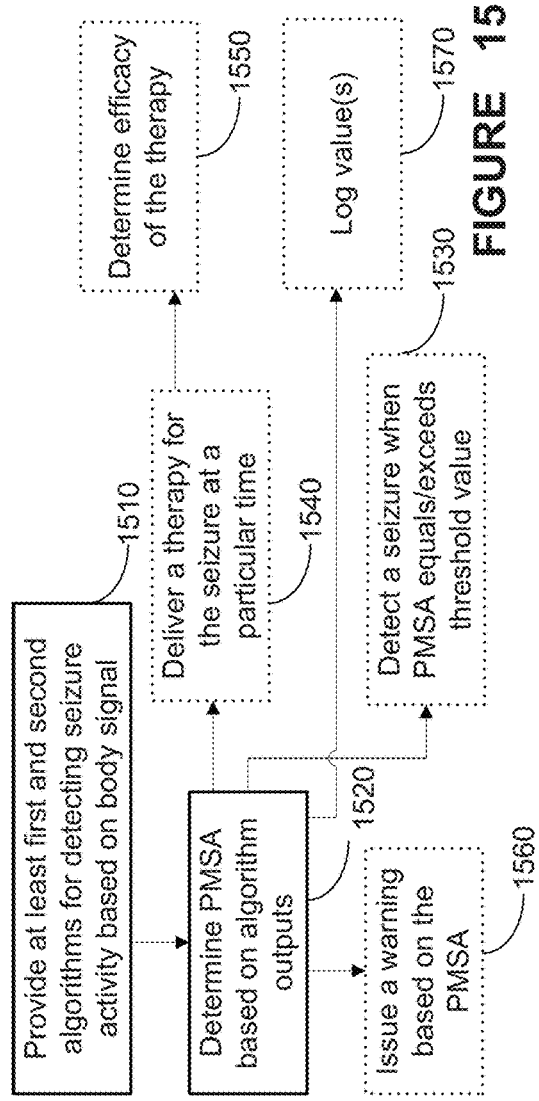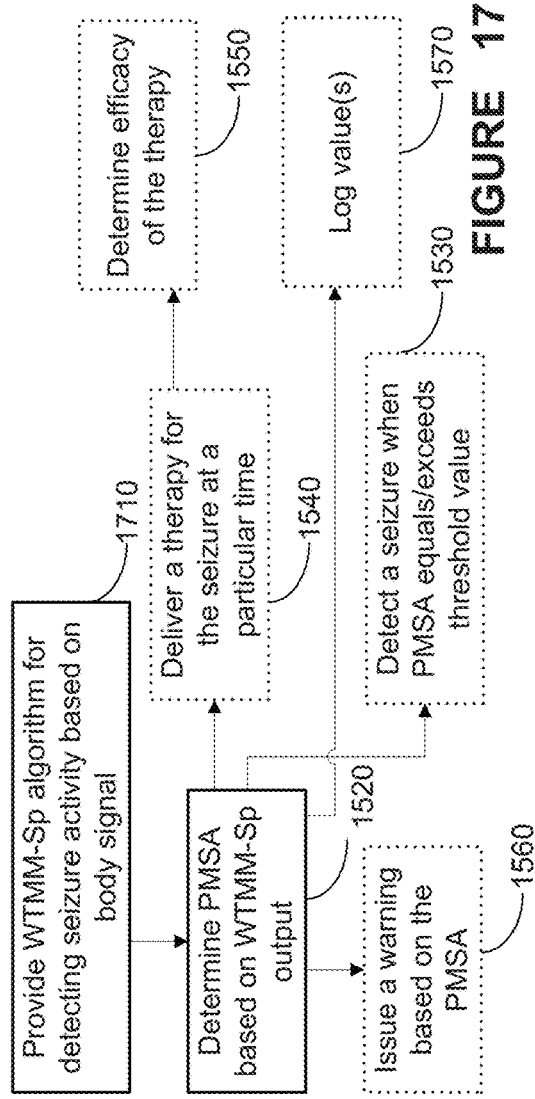

APPARATUS AND SYSTEMS FOR EVENT DETECTION USING PROBABILISTIC MEASURES

BACKGROUND OF THE INVENTION

The present application is a divisional application of and claims priority to U.S. patent application Ser. No. 13/598,339, entitled "APPARATUS AND SYSTEMS FOR EVENT DETECTION USING PROBABILISTIC MEASURES," filed on Aug. 29, 2012 which is a continuation-in-part application of and claims priority to U.S. patent application Ser. No. 13/559,116, entitled "SEIZURE DETECTION METHODS, APPARATUS, AND SYSTEMS USING A SHORT TERM AVERAGE/LONG TERM AVERAGE ALGORITHM," filed on Jul. 26, 2012 (now U.S. Pat. No. 10,537,251) which is a continuation-in-part application of and claims priority to U.S. patent application Ser. No. 13/554,367, entitled "SEIZURE DETECTION METHODS, APPARATUS, AND SYSTEMS USING A WAVELET TRANSFORM MAXIMUM MODULUS ALGORITHM," filed on Jul. 20, 2012 (now U.S. Pat. No. 9,549,677) which is a continuation-in-part application of and claims priority to U.S. patent application Ser. No. 13/554,694, entitled "SEIZURE DETECTION METHODS, APPARATUS, AND SYSTEMS USING AN AUTOREGRESSION ALGORITHM," filed on Jul. 20, 2012 (now U.S. Pat. No. 10,206,591) where each of U.S. patent application Ser. No. 13/554,367, filed Jul. 20, 2012; Ser. No. 13/554,694, filed Jul. 20, 2012; and Ser. No. 13/559,116, filed Jul. 26, 2012; all of which claim priority from provisional patent application 61/547,567 filed on Oct. 14, 2011. Each application named in this paragraph is hereby incorporated herein by reference.

1. FIELD OF THE INVENTION

The present invention relates generally to the field of biological events detection. More particularly, it concerns epileptic event detection by use of a plurality of algorithms operating on a time series of patient body signal data.

2. DESCRIPTION OF RELATED ART

There have been various advancements in the area of seizure detection, which remains a fairly subjective endeavor. The task of automated detection of epileptic seizures is generally related to and dependent on the definition of what is a seizure, definition which to date is subjective and thus inconsistent within and among experts. The lack of an objective and universal definition not only complicates the task of validation and comparison of detection algorithms, but possibly more importantly, the characterization of the spatio-temporal behavior of seizures and of other dynamical features required to formulate a comprehensive epilepsy theory.

The current state of automated seizure detection is, by extension, a reflection of the power and limitations of visual analysis, upon which it rests. The subjectivity intrinsic to expert visual analysis of seizures and its incompleteness (it cannot adequately quantify or estimate certain signal features, such as power spectrum) confound the objectivity and reproducibility of results of signal processing tools used for their automated detection. What is more, several of the factors, that enter into the determination of whether or not certain grapho-elements should be classified as a seizure, are non-explicit ("gestalt-based") and thus difficult to articulate, formalize and program into algorithms.

Most, if not all, existing seizure detection algorithms are structured to operate as expert electroencephalographers. Thus, seizure detection algorithms that apply expert-based rules are at once useful and deficient; useful as they are based on a certain fund of irreplaceable clinical knowledge and deficient as human analysis biases propagate into their architecture. These cognitive biases which pervade human decision processes and which have been the subject of formal inquiry are rooted in common practice behaviors such as: a) The tendency to rely too heavily on one feature when making decisions (e.g., if onset is not sudden, it is unlikely to be a seizure because these are paroxysmal events); b) To declare objects as equal if they have the same external properties (e.g., this is a seizure because it is just as rhythmical as those we score as seizures) or c) Classify phenomena by relying on the ease with which associations come to mind (e.g., this pattern looks just like the seizures we reviewed yesterday).

Seizure detection algorithms' discrepant results make attainment of a unitary or universal seizure definition ostensibly difficult; the notion that expert cognitive biases are the main if not only obstacle on the path to "objectivity" is rendered tenuous by certain results. These divergences in objective and reproducible results may be attributable in part, but not solely, to the distinctiveness in the architecture and parameters of each algorithm. The fractal or multi-fractal structures of seizures accounts at least in part for the differences in results and draws attention to the so-called "Richardson effect". Richardson demonstrated that the length of borders between countries (a natural fractal) is a function of the size of the measurement tool, increasing without limit as the tool's size is reduced. Mandelbrot, in his seminal contribution "How long is the coast of Britain," stressed the complexities inherent to the Richardson effect, due to the dependency of particular measurements on the scale of the tool used to perform them. Although defining seizures as a function of a detection tool would be acceptable, this approach may be impracticable when comparisons between, for example, clinical trials or algorithms are warranted. Another strategy to bring unification of definitions is to universally adopt the use of one method, but this would be to the detriment of knowledge mining from seizure-time series and by extension to clinical epileptology.

To date, performance comparisons among myriad existing algorithms have not been performed due to lack of a common and adequate database, a limitation that this invention addresses. However, if and when undertaken, said "comparisons" would be largely unwarranted and have meager, if any, clinical value/translatability, given that no universally accepted definition of what is a "seizure" has been crafted. The process of evaluation of seizure detection algorithms is plagued with cognitive biases and other confounding intricacies that impede achievement of consensus and in certain cases even of majority agreement. Performance assessment of these seizure detection algorithms relies entirely on expert visual analysis, which provides the benchmarks (seizure onset and end times) from which key metrics (detection latency in reference to electrographic and clinical onset time ("speed of detection"), sensitivity, specificity and positive predictive value) are derived, the effects of cognitive biases propagate beyond the seizure/non-seizure question into other aspects of the effectiveness of a particular seizure detection algorithm.

SUMMARY OF THE INVENTION

In one embodiment, the present disclosure provides a method of detecting a seizure in a patient, comprising:

providing at least first and second seizure detection algorithms for detecting seizure activity based upon at least one body signal; and determining a probabilistic measure of seizure activity (PMSA) value based upon the outputs of said at least first and second seizure detection algorithms.

In one embodiment, the present disclosure provides a method of detecting a seizure, comprising: determining a probabilistic measure of seizure activity (PMSA) value based upon at least a first body signal received by a first sensor and a second body signal received by a second sensor.

In one embodiment, the present disclosure provides a method of detecting a seizure in a patient, comprising: providing a wavelet transform maximum modulus-stepwise approximation (WTMM-Sp) algorithm for detecting seizure activity based upon at least one body signal; and determining a probabilistic measure of seizure activity (PMSA) value based upon said WTMM-Sp algorithm output.

In one embodiment, the present disclosure provides a method, comprising: using a first seizure algorithm for detecting a seizure activity based upon a first body signal; using a second seizure algorithm for detecting said seizure activity based upon a second body signal; and determining a probabilistic measure of seizure activity (PMSA) value based upon the outputs of said at least first and second seizure detection algorithms.

In one embodiment, the present disclosure provides a medical device comprising one or more elements configured to implement one or more steps of a method referred to above.

In one embodiment, the present disclosure provides a non-transitive, computer readable program storage device comprising instructions that, when executed by a processor, perform a method referred to above.

BRIEF DESCRIPTION OF THE DRAWINGS

The invention may be understood by reference to the following description taken in conjunction with the accompanying drawings, in which like reference numerals identify like elements, and in which:

FIG. 12. Empirical "tail" of the conditional probability distribution functions for: (a) Seizure durations (minimum duration: 2 sec); (b) the logarithm of seizure energy as estimated with the four different methods (Validated: Red; Short/Long Term Average: Blue, Auto-regressive model: Green; Wavelet Transform Maximum Modulus: Black).

FIG. 15 provides a flowchart depiction of a method, in accordance with one aspect of the present disclosure;

FIG. 16 provides a flowchart depiction of a method, in accordance with one aspect of the present disclosure;

FIG. 17 provides a flowchart depiction of a method, in accordance with one aspect of the present disclosure.

DESCRIPTION OF ILLUSTRATIVE EMBODIMENTS

Figure 1:
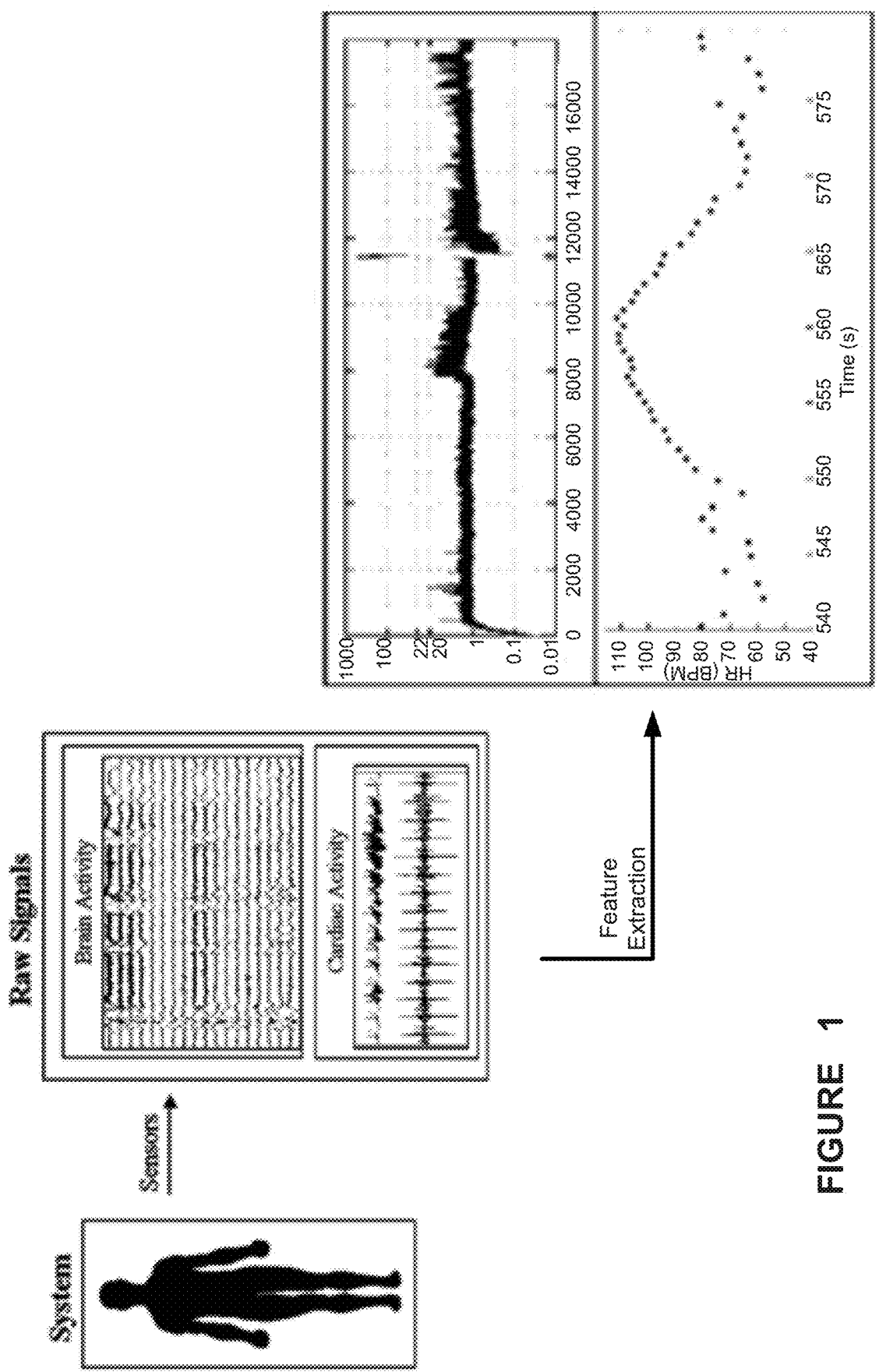
FIG. 1 illustrates a medical device system for detecting and classifying seizure events related to epilepsy from sensed body data processed to extract features indicative of aspects of the patient's epilepsy condition.

In one aspect, the present disclosure provides several new seizure detection algorithms that may be applied to one or more streams of body data. Some of these algorithms rely principally on power variance for detection of seizures, while others rely mainly on power spectral shape.

In another aspect, the present disclosure exploits the simultaneous application of two or more seizure detection algorithms to derive a probabilistic measure of seizure activity (PMSA), which may be used to issue detections with a certain probability based on multiple inputs to a probability function. The multiple inputs may be outputs from one or more seizure detection algorithms and/or one algorithm operating on two or more data streams each relating to a body signal. These algorithms include, but are not limited to, the seizure detection algorithms referred to in the previous paragraph. Other detection algorithms may be applied to various cerebral (e.g., chemical, thermal, optical) or body signals such as, autonomic (e.g., cardio-vascular, respiratory), metabolic (e.g., lactic acid, arterial pH, free radicals, endocrine (e.g., prolactin, cortisol) as required by the task at hand. This multi-algorithm, multi-modal, or multi-signal approach provides comprehensive spatio-temporal information about the dynamics/behavior of an event (epileptic seizures in the preferred embodiment) by allowing determination of the degree or extent of corporal impact (of a seizure) as well as the sequence and severity of involvement, thus expanding the state of the art that focuses only on the brain. The multi-signal approach is rooted in the observations that seizures may also affect the cardiovascular, respiratory, metabolic, endocrine, and/or musculo-skeletal systems, and that acquiring and analyzing their signals (instead of or in addition to cerebral ones) may serve to validate probabilistically a detection.

The number and properties of algorithms applied to a body signal, the number and type of body signals (e.g., cerebral/neurologic, autonomic, endocrine), the type of probabilistic measure of seizure activity, (e.g., average or product indication functions to be defined below), and their value selected for issuing event detections depend on the history and clinical status of the patient, the class, severity and frequency of seizures, the activity the patient will be engaging in, or is engaged at the time an event is presumptively detected, the extent and rapidity of spread within the brain and to other organs, the efficacy of therapies, and the time they take to reach their target, in turn determine the "optimal" detection speed, sensitivity, specificity required for the abatement of seizures control and prevention of injuries. Real-time ("on the run") automated seizure detection provides the only means through which contingent warning to minimize risk of injury to patients, delivery of a therapy for control of seizures, or logging of the date, time of onset and termination and severity may be performed.

This disclosure: a) Draws attention to the intricacies inherent to the pursuit of a universal seizure definition even when powerful, well understood signal analysis methods are utilized to this end; b) Identifies this aim as a multi-objective optimization problem and discusses the advantages and disadvantages of adopting or rejecting a unitary seizure definition; c) Introduces a Probabilistic Measure of Seizure Activity to manage this thorny issue.

Seizure detection belongs to a class of optimization problems known as "multi-objective" due to the competing nature between objectives; improvements in specificity of detection invariably degrade sensitivity and vice-versa. Attempts to achieve a universal seizure definition using objective, quantitative means, are likely to be fraught with similar competing objectives, but imaginative application of tools from the field of multi-objective optimization, among others, are likely to make this objective more tractable.

Achieving a unitary seizure definition would be difficult, as consensus among epileptologists as to what graphoelements are classifiable as ictal, is rare. In the absence of a universal definition, issuing seizure warnings for certain cases will be problematic and unsafe. For example, if a patient with seizures wishes to operate power equipment or a motor vehicle, the absence of a universal agreement on when the patient has had a seizure may preclude any viable way of ensuring, using seizure detection algorithms, that the patient's seizures are under sufficient control to allow such activities to occur. To manage the difficulties of a consensus seizure definition, substantive gains are feasible through steps entailing, for example, the application of advanced signal analysis tools to ECoG, to hasten the identification of properties/features that would lead to the probabilistic discrimination of seizures from non-seizures with worthwhile sensitivity and specificity for the task at hand. However, to even have a modicum of success, such an approach should not ignore the non-stationarity of seizures and, should strike some sort of balance between supervised (human) and unsupervised (machine-learning) approaches. The resulting multidimensional parameter space, expected to be broad and intricate, may also foster discovery of hypothesized (e.g. pre-ictal) brain sub-states.

The challenges posed by the attempt to define seizures unitarily using objective means (distinct from visual analysis) may be partly related to their fractal properties and understood through a simplistic analogy to the so-called "Richardson effect". A revision of the time-honored subjective definition of seizures may be warranted to further advance epileptology.

The present inventors propose a Probabilistic Measure of Seizure Activity (PMSA) as one possible strategy for characterization of the multi-fractal, non-stationary structure of seizures, in an attempt to eschew the more substantive limitations intrinsic to other alternatives.

The PMSA may make use of "indicator functions" (IFs) denoted xalgo for each algorithm 'algo.' Generally speaking, an IF returns a binary result of 0 (no seizure) or 1 (seizure). The IFs may then be used to prepare a function that quantifies the degree of concordance between algorithms. In one embodiment, the PMSA may make use of an Average Indicator Function (AIF). In one embodiment, the AIF is defined as:

$$AIF(t) = (X_{Val}(t) + X_{r2}(t) + X_{STA/LTA}(t) + X_{WTMM}(t))/4$$

The subscripts Val, r2, STA/LTA and WTMM refer to four different algorithms, particular embodiments of which are described herein and/or in other related applications. One or more of these algorithms may be used to detected seizures from one or more body data streams including, but not limited to, a brain activity (e.g., EEG) data stream, a cardiac (e.g., a heart beat) data stream, and a kinetic (e.g., body movement as measured by an accelerometer) data stream.

"Val" refers to an algorithm for seizure detection using ECoG data that has been validated by experts without reaching a universal consensus about its performance (e.g., false positive, false negative and true positive detections). An "r2" algorithm may also be referred to herein as an "r/\2," "autoregression," or "autoregressive" algorithm. A "STA/LTA" algorithm refers to an algorithm characterized by the ratio of a Short-Term Average to a Long-Term Average. A "WTMM" algorithm refers to a Wavelet Transform Maximum Modulus algorithm.

For determination of an AIF from the foregoing formula, an algorithm's IF equals 1 for time intervals (0.5 sec in this application) "populated" by ictal activity and 0 by inter-ictal activity. The IF's are used to generate four stepwise time functions, one for each of: a) a 2ndorder auto-regressive model (r2); b) the Wavelet Transform Maximum Modulus (WTMM); c) the ratio of short-to-long term averages (STA/LTA) and d) a Validated algorithm (Val). With these IFs, the AIF is computed (its values may range between [0-1] with intermediate values of 0.25, 0.5 and 0.75 in this embodiment). (Intermediate AIF values are functions of the number of algorithms applied to the signal. Since in this study 4 methods were used and the range of the indicator function is [0-1], the intermediated values are [0.25, 0.5, 0.75]). These values [0-1] are estimates of the probability of seizure occurrence at any given time. In another embodiment, the values of each algorithm's IF may be weighted differently, and a composite IF (e.g., a Weighted Indicator Function or WIF) different from the AIF may be computed.

Human Seizure Time Series/ECoG

Data obtained from one subject undergoing evaluation for epilepsy surgery with intra-cranial electrodes was selected for analyses as it had the largest number of clinical and subclinical seizures in the University of Kansas Medical Center Epilepsy Database. ECoG was collected in accordance with the Center's surgical evaluation protocol and with the Human Subjects Committee requirements, which include signing of a consent form by the subject.

The ECoG was recorded using electrodes implanted into the amygdala, pes hippocampus and body of hippocampus bilaterally through the temporal neocortex and had a duration of 6.9 days (142'923'853 samples; 239.75 Hz sampling rate).

Differentiation of the ECoG Signals Used in the Analyses

Figure 13:
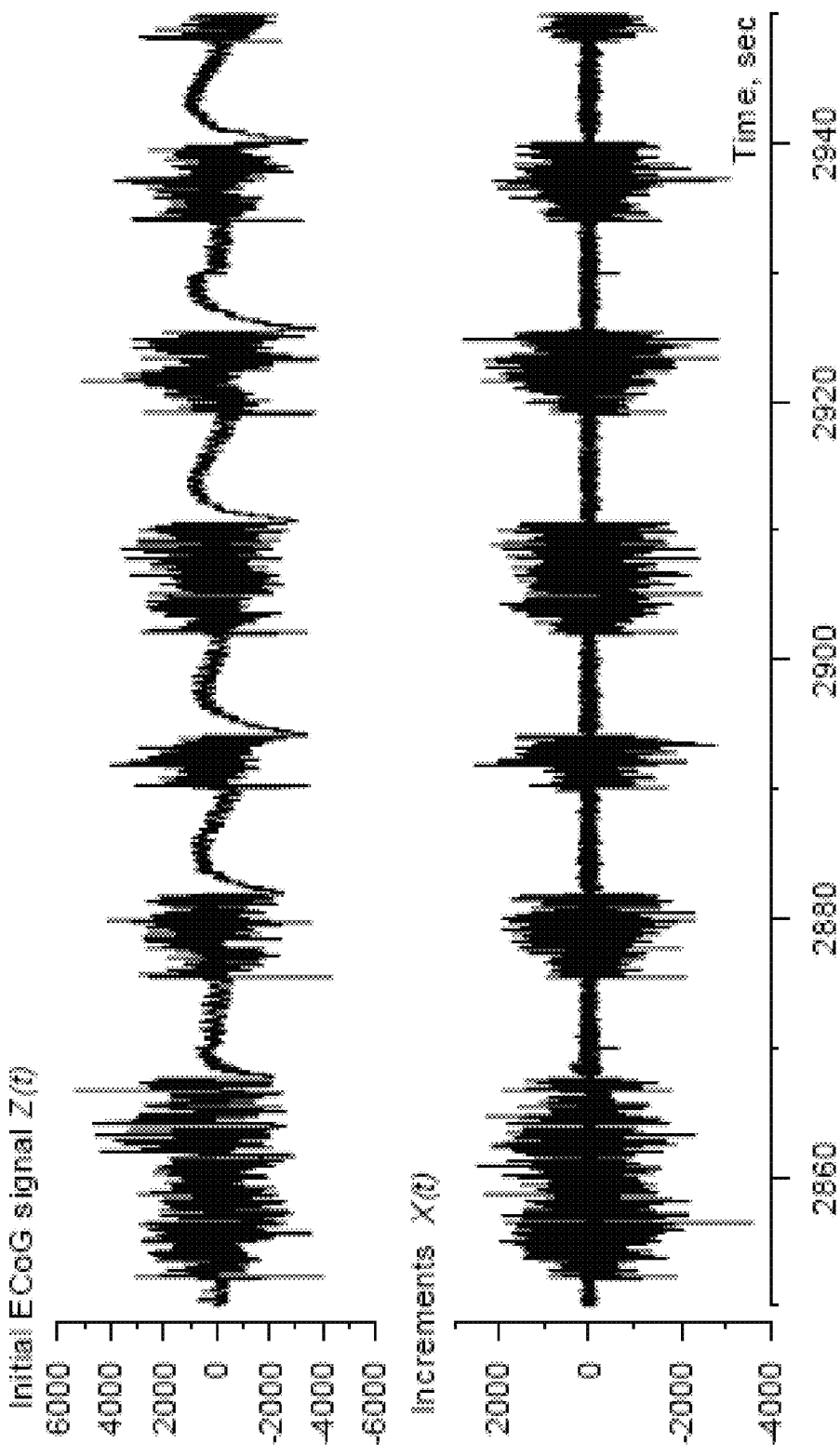
FIG. 13. ECoG before (upper panel) and after differentiation (lower panel).
Figure 14:
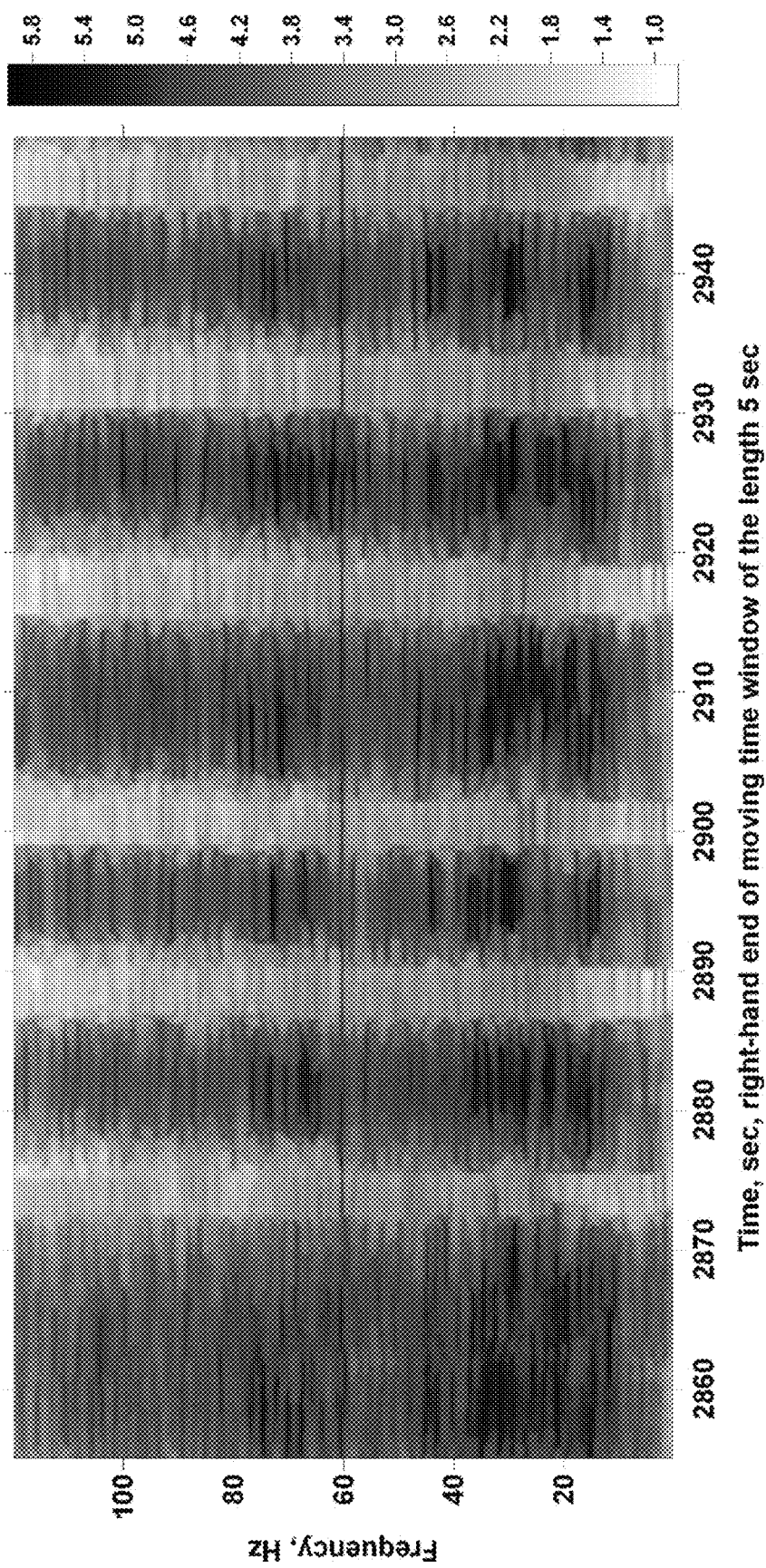
FIG. 14. Temporal evolution of the decimal logarithm of the power spectrum of differentiated ECoG (as shown in FIG. 13, bottom panel) estimated in 5 s moving windows.

For efficient analyses, ECoG signal differentiation was performed, so as to minimize the non-stationarity present in them. If $Z(t)$ is raw ECoG, then its difference is $X(t)=Z(t)-Z(t-1)$ where (t) corresponds to a sample time increment. This linear operation is exactly invertible and, unlike band-pass filtering or detrending, does not suppress low frequency fluctuations, but decreases their overall influence. FIG. 13 illustrates the effect of this operation on raw ECoG. The differentiated ECoG is less non-stationary (chiefly at low frequencies) than the undifferentiated one (x-axis: time in sec.; y-axis: amplitude in microvolts). FIG. 14 shows a time-frequency map of the evolution of the power spectra of differentiated ECoG segments. The power spectra are estimated within 5 sec moving windows of length. Six brief seizures appear as marked power spectrum increases (red and specks of white) in the 10-100 Hz. band (x-axis: time in sec.; y-axis: frequency (Hz); color scale to the right of main graph).

Seizure Detection Methods

The following signal analysis methods were applied to the electrocorticogram (ECoG) to derive metrics for the discrimination of seizure from non-seizure signals:
(i) An Auto-Regression (AR) model of the 2nd order, yielding autoregression coefficients and the logarithm of residual variance,
(ii) Estimates of the logarithm of the standard deviation (SD) of differentiated ECoG using long chains of wavelet transform modulus maxima (WTMM chains) based on the first derivative of a Gaussian function $\sim\exp(-t^2)$ as a continuous wavelet kernel, and
(iii) The ratio of the "short time average" (STA) to the "long time average" (LTA), widely used in seismology for precise real-time earthquake detection. The spectral and dynamical similarities between seizures and earthquakes provide the motivation for application of this method to epileptology.
(iv) A validated seizure detection algorithm used as a reference to better interpret the results of the novel proposed ones and to cast light on the intricacies and challenges of discriminating seizure from non-seizure signals even when using objective, quantitative means.

The use of autoregression, WTMM, STA/LTA, and the validated methods for detecting seizure from body signal data is described in more detail in U.S. patent applications {13/554,694, filed Jul. 20, 2012, Ser. No. 13/554,367, filed Jul. 20, 2012, and Ser. No. 13/559,116, filed on Jul. 26, 2012, all of which are incorporated herein by reference.

Results

The dependencies of AIF values on the detection algorithm applied to the ECoG are illustrated in FIG. 6A-D. The AIF value (0-1) of this function is calculated based on the output of each of the four detection algorithms used and reflects the probability that grapho-elements are ictal in nature; the higher the AIF value, the greater the probability that the detection is a seizure. AIF values of 1 (the activity is detected by all algorithms as a seizure) or 0 (none of the algorithms classifies the grapho-elements as a seizure) pose no ambiguity, but as shown in this study, are likely to be less prevalent than intermediate values [0<AIF<1]. As shown in FIG. 6, the larger amplitude, longer oscillations are the only ones to have an AIF value of 1, indicative of "consensus" among all detection algorithms (x-axis: time; y-axis: AIF values). By way of example, cortical activity may be classified as a seizure if the AIF value is 0.75, having been detected by the majority (¾) of methods. In examples presented herein, four different methods (r2, WTMM, STA/LTA, and Val) were investigated, but this number may vary according to the task at hand; for warning for the purpose of allowing operation of a motor vehicle, application of a larger number of detection algorithms to cortical signals and an AIF value of 1 would be desirable while, for automated delivery of an innocuous, power inexpensive therapy, less algorithms and much lower AIF values would be tolerable.

Figure 7:
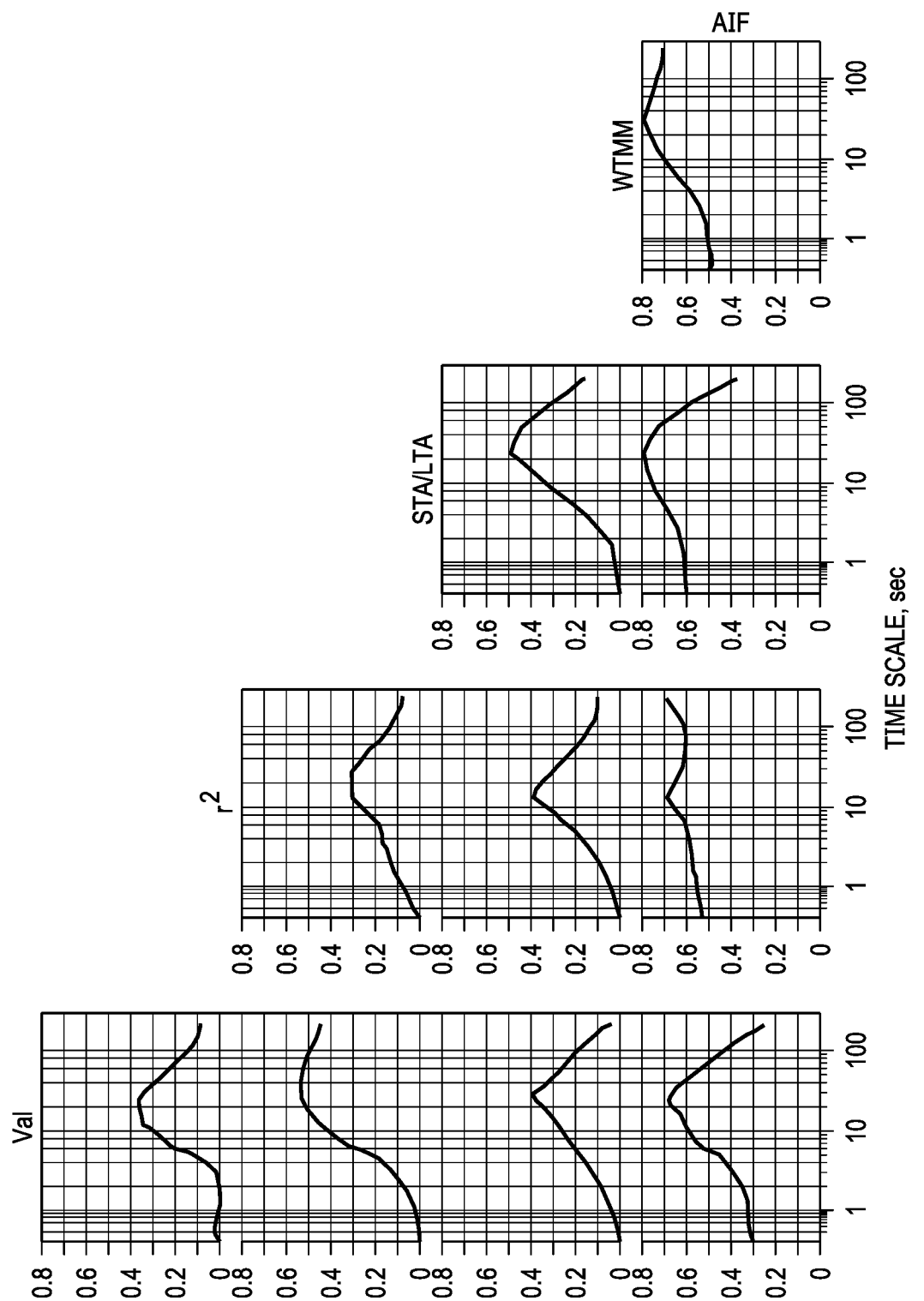
FIG. 7. Plots of time scale-dependent correlations between Haar wavelet coefficients of the indicator functions (IFs), between pairs of detection methods and between each method and the averaged indicator function (AIF).
Figures 8A, 8B:
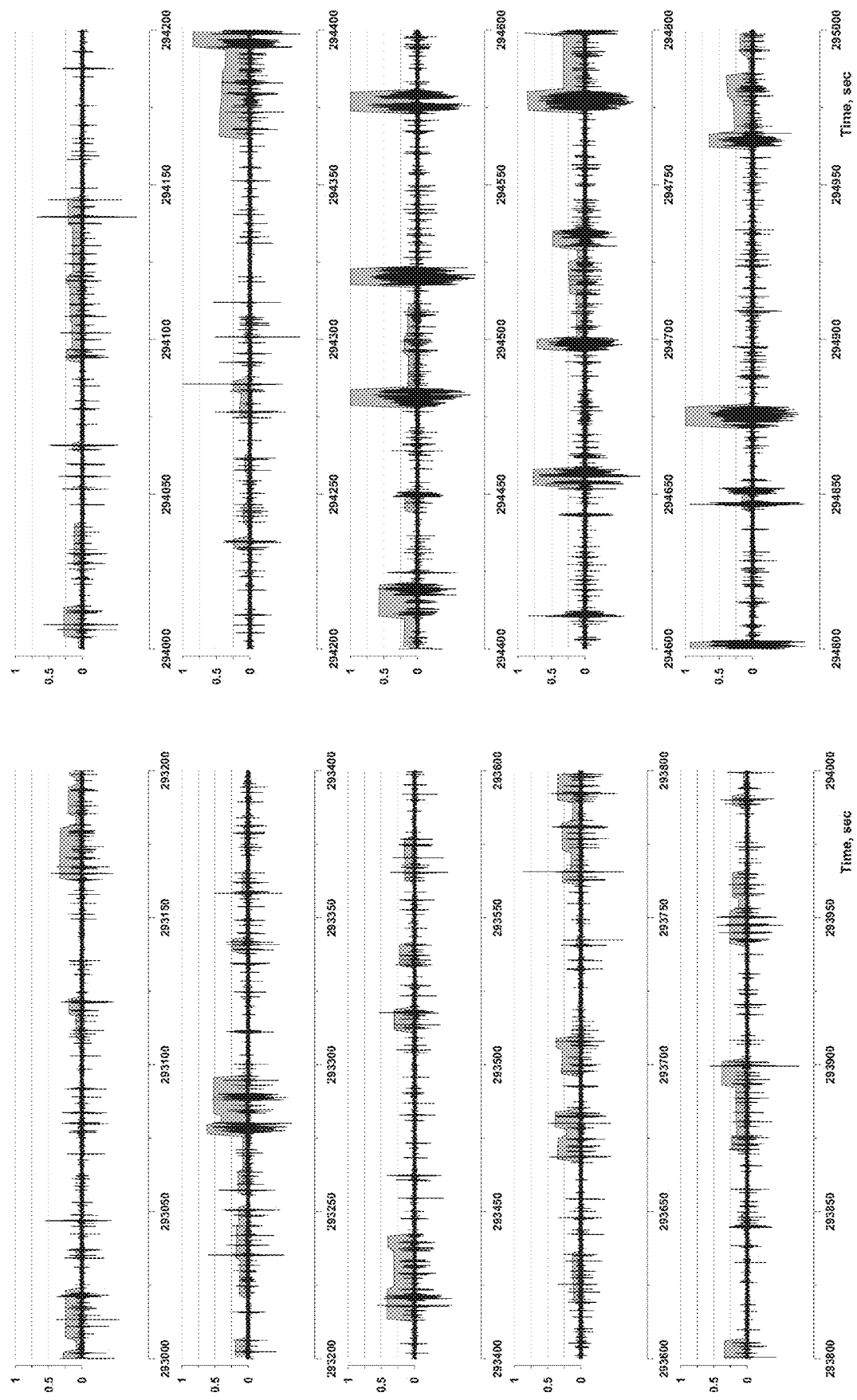
FIG. 8a-d. Probability Measure of Seizure Activity estimated using the Wavelet Transform Maximum Modulus—Stepwise Approximations.
Figures 8C, 8D:
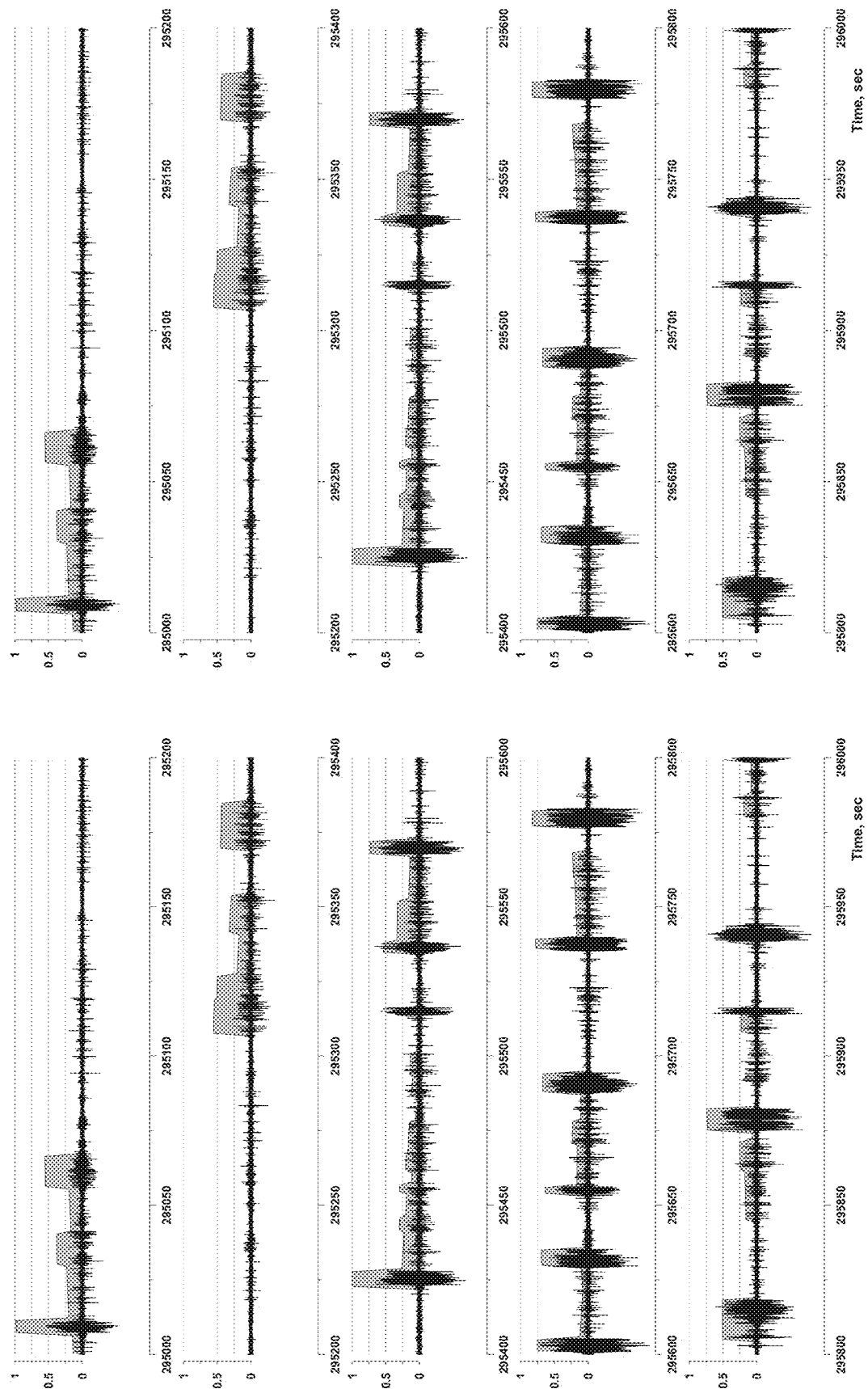

The cross-correlation between each pair of algorithm's IF and their average function (AIF) were calculated; since each of these is a step function (see FIG. 6), the Haar wavelet transform was applied to them to facilitate visualization of their value (y-axis) as a function of this wavelet's logarithmic time scale (x-axis (FIG. 7)). In FIG. 7, r2, STA/LTA and WTMM act as labels for both columns (label on top) and rows (label to the right of each row), whereas Val designates only the column below it and AIF the row to its left. FIG. 7 may be viewed as the lower half of a square matrix; this triangle's vertices are: the top left-most plot depicts the correlation between Val and r2, the bottom left-most plot the correlation between Val and AIF and the bottom right-most graph, that between WTMM and AIF; all other correlations lie within these vertices (y-axes: Correlation values; x-axes: Logarithmic time scale). The correlations (indicative of the concordance level) between each IF pair and between each method's IF and the AIF, increases monotonically, reaching a maximum between 20-30s, after which they decrease also monotonically (except for AIF vs. r2): The WTMM and r2 methods have the highest correlations with AIF for time scales exceeding 100 sec. Since estimating the probability measure of seizure activity based on the AIF requires the output of at least two detection algorithms, a simpler approach is to apply only one, a Wavelet Transform Maximum Modulus-Stepwise Approximation (WTMM-SAp).

Let $U(\xi_j)$ be a logarithm of the standard deviation of differentiated ECoG computed within "small" adjacent time windows of length L and $\xi_j$ the time moments corresponding to right-hand ends of these windows. Thus, $\xi_j$ values are given within the step $L \cdot \delta t$, where $\delta t$ is an ECoG time interval.

Let $S_U(\xi|a_*^{(j)})$ be a WTMM-SAp computed for the dyadic sequence of m dimensionless scale thresholds:

$$a_*^{(j)} = a_*^{(0)} \cdot 2^{(j-1)}, j=1,\ldots,m \qquad (26)$$

and $S_U^{(a)}(\xi)$ be their mean value:

$$S_U^{(a)}(\xi) = \sum_{j=1}^{m} S_U(\xi|a_*^{(j)})/m \qquad (27)$$

The averaged WTMM-SAp $S_U^{(a)}(\xi)$ may reveal abrupt changes of $U(\xi_j)$ for different scales (the use of a dyadic sequence (26) suppresses "outliers"). The background is estimated by a simple average within a moving time window of the radius of n discrete values of J:

$$\overline{S}_U^{(a)}(\xi_j) = \sum_{k=-n}^{n} S_U^{(a)}(\xi_{j+k})/(2n+1) \qquad (28)$$

Seizures correspond to positive peaks of above background $\overline{S}_U^{(a)}(\xi)$. Thus, the values:

$$\Delta S_U^{(a)}(\xi) = \max\{0, S_U^{(a)}(\xi) - \overline{S}_U^{(a)}(\xi)\} > 0 \qquad (29)$$

are regarded as a Measure of Seizure Activity (MSA). In order to make this measure probabilistic (PMSA), consider an empirical probability distribution function:

$$F_{\Delta S_U^{(a)}}(X) = Pr\{\Delta S_U^{(a)}(\xi) < X\} \qquad (30)$$

and let $Q_{\Delta S_U^{(a)}}(\gamma)$ be the γ-quantile of the function (30), i.e. the root of the equation:

$$F_{\Delta S_U^{(a)}}(Q) = 1-\gamma, 0 < \gamma < 1 \qquad (31)$$

The PMSA is defined by the formula:

$$\mu(\xi) = \min\{\Delta S_U^{(a)}(\xi), Q_{\Delta S_U^{(a)}}\gamma\}/Q_{\Delta S_U^{(a)}}(\gamma), 0 \le \mu(\xi) \le 1 \qquad (32)$$

It should be underlined that the PMSA (32) is defined within sequences of "small" time intervals of length L−δt and $\xi = \xi_j$ are discrete time values, corresponding to right-hand ends of these time windows.

The method of constructing a PMSA based on the WTMM-SAp utilizes the following parameters whose values are shown in parentheses: The number L of adjacent samples for computing the logarithm of the standard deviations $U(\xi_j)$ for differentiated ECoG increments (L=240).

The values of $a_*^{(0)}$, m for setting the dyadic sequence of WTMM scale thresholds in the formula (26) ($a_*^{(0)}$=5 m=6, e.g., the following scale thresholds were used: 5, 10, 20, 40, 80 and 160).

The number n of $\xi_j$ values for the radius of the moving averaging in formula (28) (n=200, e.g., for L=240 and 1/δt=239.75 Hz, the averaging length within formula (28) equals 401 sec).

The probability level Y for calculating a quantile in formula (31) (γ=0.01)

Figure 9:
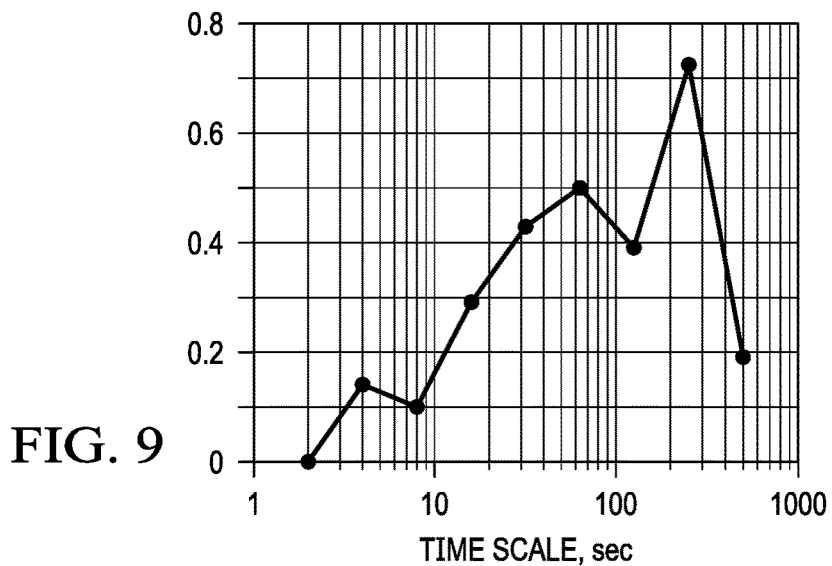
FIG. 9. Graphic of time scale-dependent correlations between PMSA-AIF and PMSA-SA after smoothing of their step-wise functions with Haar wavelets.

FIG. 8a-d represent PMSA estimates using WTMM-Sp performed on the same data as used in the PMSA estimates of FIG. 6a-d. The oscillations in black are cortical activity and the grey stepwise function, the probability value they correspond to seizures (x-axes: time; y-axes PMSA values). The results of the estimations of PMSA using WTMM-SAp (FIG. 8) differ in one aspect (lower number of events with probability 1) from those obtained with the PMSA-AIF, given the dissimilarities between these two approaches, but are alike in uncovering the dependencies of PMSA on seizure duration: in general, the shorter the duration of a detection, the larger the discordance between detection methods, a "trait" that interestingly, is also shared by expert epileptologists. Inter-algorithmic concordance as evidenced by the cross-correlation values between PMSA-WTMM-SAp and PMSA-AIF (FIG. 9) grow quasi-linearly (albeit non-monotonically) with the temporal length of seizures. The correlation value increases as a function of time, reaching a maximum value (0.73) at about 250 s, before decaying steeply thereafter. Worthy of comment is the decay in cross-correlation values for seizure exceeding a certain length for both PMSA-AIF and PMSA-WTMM-SAp.

The crafting of, or "convergence" towards, a unitary seizure definition would be epistemologically expensive and may thwart/delay deeper understanding of the dynamics of ictiogenesis and of the spatio-temporal behavior of seizures at relevant time-scales. In the absence of a universal definition, substantive gains are feasible through steps entailing, for example, the application of advanced signals analyses tools to ECoG, to hasten the identification of properties/features that would lead to the probabilistic discrimination of seizures from non-seizures with worthwhile sensitivity and specificity for the task at hand. Tools such as those available through cluster analysis of multidimensional vectors of relevant features would aid in the pursuit of automated seizure detection and quantification. To even have a modicum of success, this approach should not ignore the non-stationarity of seizures and strike some sort of balance between supervised (human) and unsupervised machine-learning) approaches. The resulting multidimensional parameter space, expected to be broad and intricate, may also foster discovery of hypothesized (e.g. pre-ictal) brain sub-states.

The total number of detections, their duration and the percent time spent in seizure over the time series total duration (6.9 days) are presented in Table 1.

TABLE 1

Summary statistics obtained by applying four different detection methods (Validated Algorithm; $r^2$; STA/LTA; WTMM) to a prolonged human seizure time-series. The minimum duration of seizures was set at 2 s because such duration is the minimum possible for the WTMM method with the parameter L = 240.

|  | Validated algorithm | $r^2$ | STA/LTA | WTMM |
|---|---|---|---|---|
| Total number of seizures with duration ≥2 s. | 3184 | 7029 | 16275 | 10795 |
| Mean duration, s. | 3.8 | 23 | 4.3 | 18.6 |
| Median duration, s. | 3.4 | 7 | 3.5 | 6 |
| % time spent in seizure | 2 | 27 | 12 | 34 |

The STA LTA yielded the largest number of detections, but only the third largest time spent in seizure, given the shortness of median duration of detection compared to those computed by the WTMM and $r^2$ methods. The mean and median durations of detections issued by the $r^2$ method were the longest, but the WTMM algorithm surpassed all others in duration of time spent in seizure.

In order to better understand these differences, an indicator function (IF) is applied to the results. IF equals 1 for the duration of a seizure and 0 before its onset and after its termination (0 corresponds to non-seizure intervals as identified by each method). The calculation of the IF generates four-stepwise time functions, one for each detection method: $X_{val}(t)$, $X_{r^2}(t)$, $X_{STA/LTA}(t)$ and $X_{WTMM}(t)$. Using this IF, two additional functions are computed over a 0.1 s running window: a) The average indicator function (AIF):

$$AIF(t) = (X_{Val}(t) + X_{r^2}(t) + X_{STA/LTA}(t) + X_{WTMM}(t))/4 \qquad (23)$$

and b) The product of indicator functions (PIF):

$$PIF(t) = X_{Val}(t) \cdot X_{r^2}(t) \cdot X_{STA/LTA}(t) \cdot X_{WTMM}(t) \qquad (24)$$

The AIF's values may vary between [0-1] (and can take on any intermediate value 0.25, 0.5, 0.75 in this application) whereas the PIF values are either 0 or 1; a PIF=1 corresponds to an AIF=1 and a PIF=0, to an AIF <1. Time intervals for which AIF=PIF=1 correspond to seizures detected by all methods. Typically, AIF values are smaller than 1 (e.g., only one or two out of the four methods recognize the activity as ictal in nature) at the onset and termination of certain type of ECoG activity but frequently reach 1, sometime into the ictus as all methods "reach consensus". Table 2 provides further evidence that, at some point in time, the majority of seizures detected by the validated algorithm are also detected by the other three methods, with WTTM detecting the largest number (97%) and STA/LTA the second largest (91.5%) number of seizures. More specifically and by way of example, the value 0.971 in Table 2 means that the WTMM method detections encompass 97.1% of seizure time intervals detected with the validated method, with the exception of 1.6 s. that correspond to the delay/lag between them in detecting seizure onsets (see below for details).

TABLE 2

Values of specificity of the three novel methods calculated with respect to the validated method and time lag (as defined in the text) at which the specificities attain their largest values.

| Method | $Spe_{Method\_Val}(0)$ | $\max_\tau Spe_{Method\_Val}(\tau)$ | $\arg\max_\tau Spe_{Method\_Val}(\tau)$ |
|---|---|---|---|
| $r^2$ | 0.628 | 0.882 | −1.1 s |
| WTMM | 0.823 | 0.971 | −1.6 s |
| STA/LTA | 0.911 | 0.915 | −0.4 s |

Time intervals for which the pairwise product $X_{Val}(t) \cdot X_{r^2}(t)=1$ correspond to seizures detected by both the validated algorithm and $r^2$. Dividing the number of time intervals when $X_{Val}(t) \cdot X_{r^2}(t)=1$ by the number of intervals when $X_{Val}(t)=1$, yields the specificity of the $r^2$ method with respect to the validated algorithm. Since the validated algorithm has an inherent delay of 1 s (the median filter's foreground window is 2 s) and an additional duration constraint of 0.84 s. is imposed before a detection is issued, its onset and end times are "delayed" compared to those yielded by the other methods. To account for this delay and make comparisons more meaningful, the specificity of the $r^2$ with respect to the validated algorithm is re-calculated as a function of a time shift r.

$$Spe_{r^2\_Val}(\tau) = \sum_t (\chi_{r^2}(t+\tau) \cdot \chi_{Val}(t)) / \sum_t \chi_{Val}(t) \quad (25)$$

The specificity functions for the two other methods $Spe_{WTMM\_Val}(\tau)$ and $Spe_{STA/LTA\_Val}(\tau)$ are identically computed and their maximum value (dependent on τ) may be regarded as the mean value of the time delay of one method's function with respect to another for seizure onset and end times. From the results shown in FIG. 10, it can be seen that the time differences are negative for all methods with respect to the validated one; that is, the validated algorithm's detection times lag behind those given by the other methods. Particularly, the mean delay of the validated algorithm is 1.1 s with respect to $r^2$, 0.6 s with respect to STA/LTA and 1.6 s with respect to WTMM while the mean delay of $X_{Val}(t)$ with respect to $X_{PIF}(t)$ is 0 by construction. As expected, the re-calculated specificity values shifted by r shown in Table 2 are higher compared to those without shifting.

Figure 10:
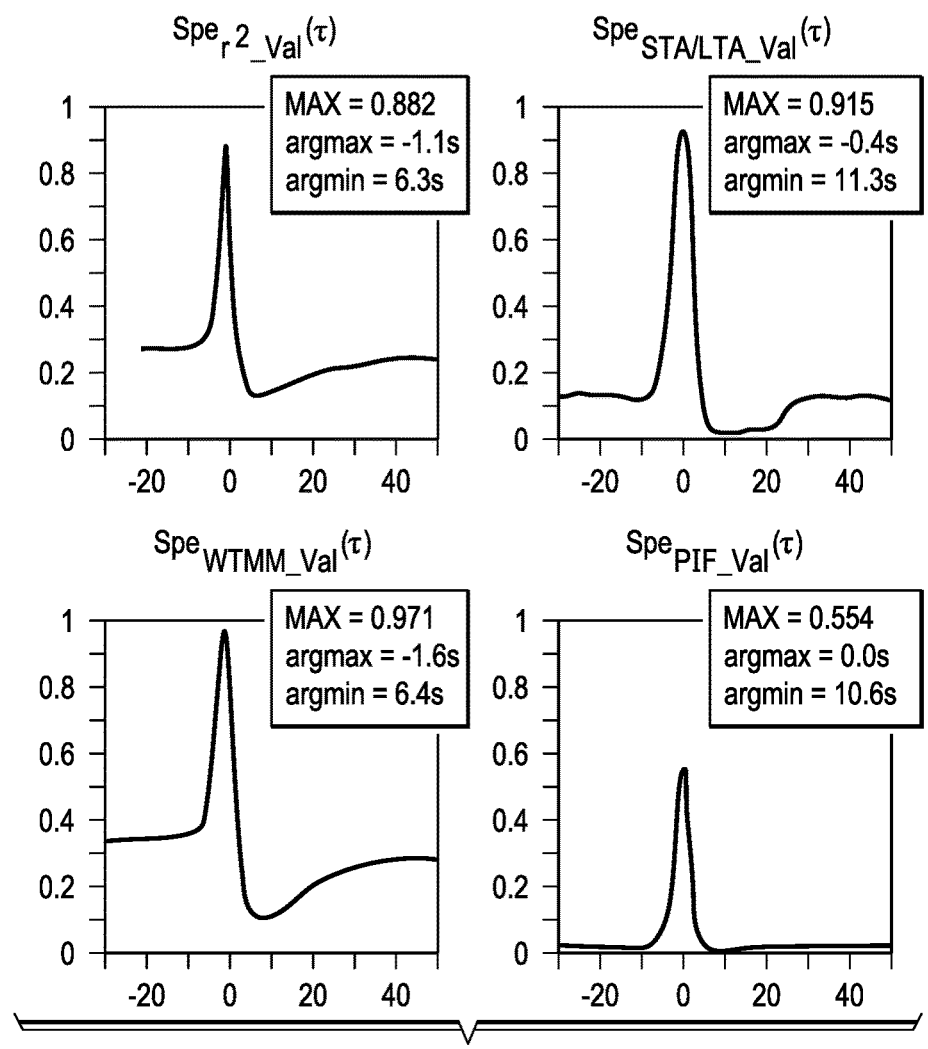
FIG. 10. Graphics of specificity functions for each method as a function of time with respect to the Validated algorithms's time of seizure detection. Upper left panel: Auto-regressive model vs. Validated algorithm; Upper right panel: Short/Long Term Average Method vs. Validated algorithm; Lower leftpanel: Wavelet transform Maximum Modulus vs. Validated algorithm; Lower right panel: Product Index Function vs. Validated algorithm.
Figure 11A:
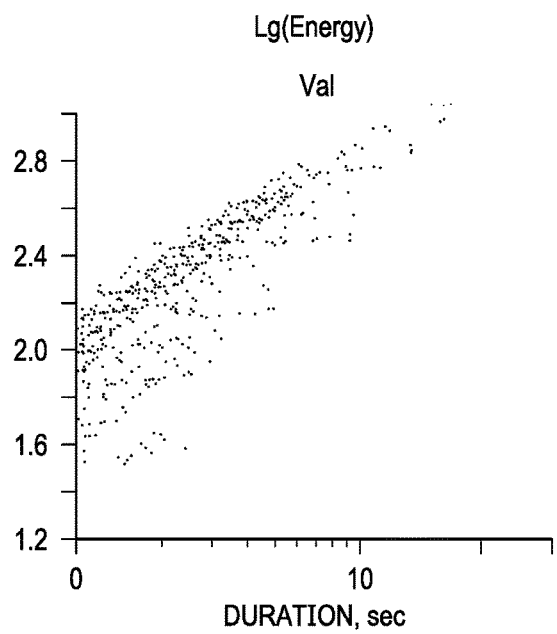
FIG. 11a-d. Plots of the decimal logarithm of the dependence of seizure energy on seizure duration (minimum duration: 2 sec.). Seizure is defined as the product of the standard deviation of the differentiated the ECoG and seizure duration (in sec.). Upper left plot: Validated algorithm detections; Right upper plot: Short/Long Term Average detections; Left lower plot: Auto-regressive model detections; Right lower plot: Wavelet-Transform Maximum Modulus detections.
Figure 11B:
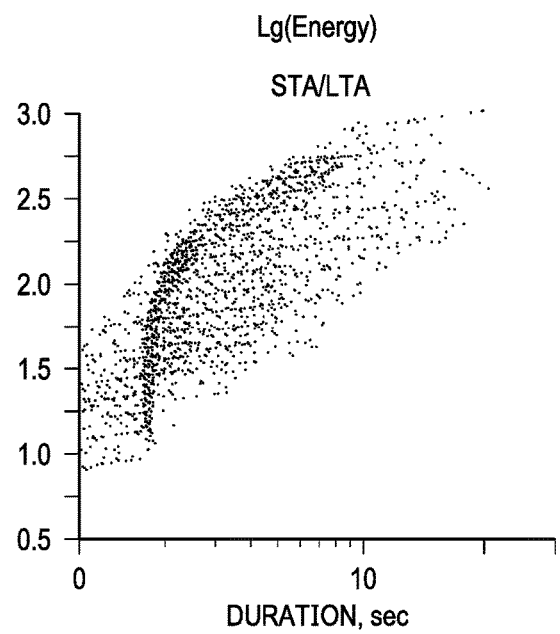
Figure 11C:
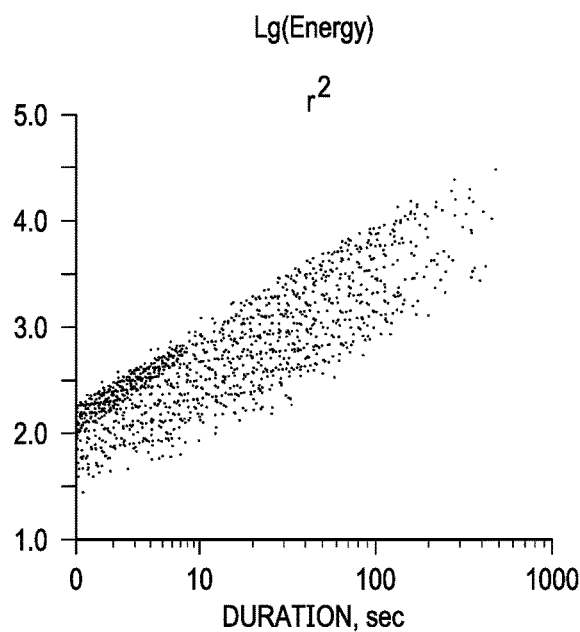
Figure 11D:
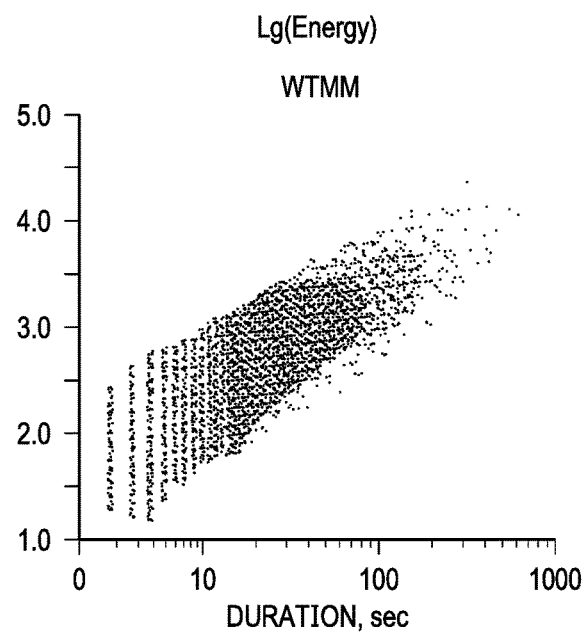

Also of note from FIG. 10 is that only 55% of seizures detected by all methods are detected by the validated algorithm (Val). Tau (r) zero (x-axis) corresponds to the time at which Val issues a detection. Negative τ values indicate "late" detections by the validated algorithm in relation to the other three and positive value the opposite. As discussed, $r^2$, STA/LTA and WTMM issue earlier detections than Val. Values of the lags τ corresponding to the maximum and minimum values of each function are presented for each graphic under the names argmax and argmin respectively.

Except for $Spe_{PIF\_Val}(\tau)$, the shape of the other specificity functions is asymmetric (FIG. 10). Negative values of the specificity functions found for small positive mutual shifts r are the consequence of the fact that, on average, these time shifts correspond to periods that the Val method does not classify as seizures, activity that the other methods do. This alternating effect for mutually shifted seizures time intervals is the strongest for the values of corresponding to the minimum of the cross-covariance functions. There are also instances when other methods do not classify some time intervals as seizures while the validated algorithm does.

The value $$\max_\tau Spe_{PIF\_Val}(\tau) = Spe_{PIF\_Val}(0) = 0.554$$

indicated in the lower right panel of FIG. 10 means that only 55.4% of seizures recognized as such by the other methods are also detected by the validated method, indicating that in its generic form and by design, it is less sensitive and more specific for seizure detection than the others.

DISCUSSION

The three methods presented herein survey different but inter-dependent ECoG signal properties, thus expanding the breadth and perhaps also the depth of insight into the spectral "structure" of epileptic seizures in a clinically relevant manner. The Auto-Regressive model ($r^2$), sensitive mainly to changes in spectral shape, was chosen as the simplest and most general method, with which to provide a statistical description of oscillations (ECoG) that may be regarded as generated by the stochastic analogue of a linear oscillator. The WTMM method is well suited for estimations of changes in power variance within adjacent "short" time windows whereas the STA LTA uses the ratio of variances to detect, at low computational expense, ECoG signal changes corresponding to seizures. The validated algorithm whose architecture is similar to that of the STA LTA and is also sensitive to power variances within certain frequencies (8-45 Hz) was used as a "benchmark" since its performance has been subject to rigorous peer-review. The $r^2$ and STA LTA algorithms are implementable into implantable devices as they operate in real-time, while the WTTM is best suited for off-line analysis applications given its relatively high algorithmic complexity.

Whereas various performance metrics for each algorithm pervade the Results section inevitably leading to comparisons among them, these would be misleading and misplaced given that each method not only operates with different parameters, but also probes different ECoG features. The discrepancies in number and duration of detections issued by each algorithm, which may be inherently or operationally "irreconcilable", parallel those that possibly characterize and define visual expert analysis. The fundamental implication of this observation is that a unified or universal "definition" of what cortical activity constitutes a seizure may not be attainable (nor desirable) even through the application of objective, advanced signal analyses methods, particularly for seizure onset and termination segments. Algorithmic and visual expert analysis consensus as to what grapho-elements define a 'seizure' seems to be highly dependent on when during the course of a 'seizure' a decision is made. In this context, it is noteworthy that AIF and PIF frequently reached a value of 1, indicative of concordance among all detection methods sometime after seizure onset and before its termination (as determined by any of the methods), provided the seizures reached a certain duration (20-30 s.) as it will be discussed in more detail in this issue's accompanying article. In short, seizure onsets and terminations may be under certain conditions universally undefinable by algorithmic or expert visual analysis. A systematic investigation of the differences in signal spectral properties between the "preface"/"epilogue" and the "main body" of seizures was not performed. It is speculated that the presence of "start-up transients" (in a dynamical sense) and of temporo-spatial dispersion of the ictal signal (which impacts S/N) may be most prominent at the onset and termination of seizures. These and local and global state-dependencies of certain signal features, account in part for the temporalfluctuations in algorithmic detection performance that characterize these results.

Defining seizure energy, as the product of the standard deviation of the power of ECoG by its duration (in seconds), reveals that the $r^2$ and WTMM methods identify as a continuum, seizures that the STA LTA and validated algorithms detect as clusters of short seizures. The lack of correspondence between a certain percentage of detections (11.8% for the $r^2$ method, 2.9% for the WTMA method and 8.5% for the STA LTA method) and the validated algorithm may be partially attributed to brief discontinuities in seizure activity. This phenomenon ("go-stop-go") appears to be inherent to seizures (e.g., it is a general feature of intermittency associated with many dynamical systems). These discontinuities are also an "artifact" caused by the architecture of and parameters used in each algorithm. For example, the longer the foreground window and the higher the order statistical filter (e.g., median vs. quartile), in the validated algorithm, the higher the probability that "gaps" in seizure activity will go occur. Clustering of detections is a strategy to manage dynamical or artifactual ictal "fragmentation".

The dependencies of seizure energy on seizure duration, for the set of icti detected by each of the methods, are depicted in FIG. 11. A subset of seizures detected by all methods obeys a simple law of proportionality between energy and duration, that is, the longer the seizure, the largest its energy. However, this relationship is far from being invariably linear, indicating the presence of interesting scaling properties of seizure energy. Indeed, with the exception of the validated method, the others detect sets of seizures that are characterized by non-trivial scaling properties and much more variability in the standard deviation of the power of cortical activity. This can be surmised from the slopes being different from 1 (FIG. 11) of the lower envelops of the scatter of points in panels (c) and (d) corresponding to the $r^2$ and WTMM methods, and to the nonlinear dark crescent seen in panel (b) corresponding to the STA LTA method. The seizures detected by the validated algorithm have the smallest dispersion in the energy-duration relation. As expected, the differences in seizure onset and termination times are reflected in the energy-duration distributions; the dispersion of standard deviations varies widely among the different methods and non-linearities are present in certain distributions (e.g., FIG. 11b).

The conditional probabilities of durations (FIG. 12a) and of the logarithm of energy of seizures (FIG. 12b) provide additional support that their properties are partly a function of the method used for their detection. The validated and STA LTA algorithms yield similar durations but different from those of the WTMM and $r^2$ methods, which are analogous to each other (FIG. 12a). The distributions of the logarithm of seizure energies as identified by each of the methods (FIG. 12b) reveals additional discrepancies as evidenced by the much narrower and shorter "tail" distribution of the validated algorithm compared to the others.

To conclude, each of the investigated methods is "sensitive" to different seizure properties or features and may be regarded as providing complementary dynamical and clinical relevant knowledge with translational value. The AIF and PIF may be viewed as a first attempt towards a more nuanced definition (probabilistic) of seizures with operational value. That concordance levels between methods fluctuates as a function of seizure duration, commonly reaching its highest possible value (AIF=PIF=1) sometime (20-30 s.) after onset, insinuate a decline in signal complexity or in its entropy, as feature homogeneity transitorily prevails over heterogeneity.

An embodiment of a medical device adaptable for use in implementing some aspects of embodiments of the present invention is provided in FIG. 1. As shown in FIG. 1, a system may involve a medical device system that senses body signals of the patient—such as brain or cardio-vascular activity—and analyzes those signals to identify one or more aspects of the signal that may identify the occurrence of a seizure. The signal may be processed to extract (e.g., mathematically by an algorithm that computes certain values from the raw or partially processed signal) features that may be used to identify a seizure when compared to the inter-ictal state. As shown in the right side of FIG. 1, the features may also be graphically displayed either in real time or subsequent to the event to enable visual confirmation of the seizure event and gain additional insight into the seizure (e.g., by identifying a seizure metric associated with the seizure).

Figure 2:
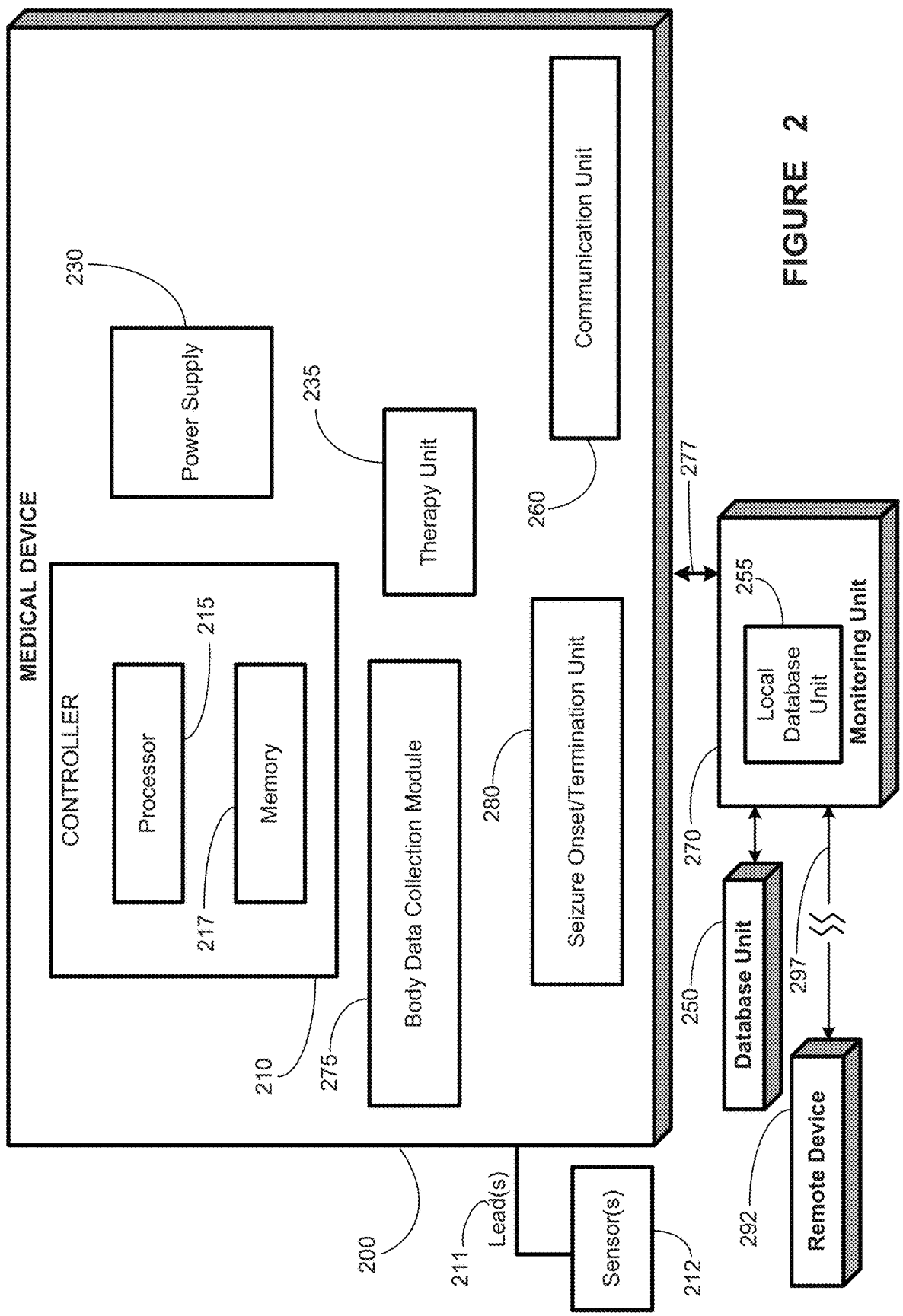
FIG. 2 provides a schematic representation of a medical device, in accordance with one aspect of the present disclosure.

Turning now to FIG. 2, a block diagram depiction of a medical device 200 is provided, in accordance with one illustrative embodiment of the present invention. In some embodiments, the medical device 200 may be implantable (such as an implantable electrical signal generator), while in other embodiments the medical device 200 may be completely external to the body of the patient.

The medical device 200 may comprise a controller 210 capable of controlling various aspects of the operation of the medical device 200. The controller 210 is capable of receiving internal data or external data, and in one embodiment, is capable of causing a therapy unit 235 to generate and deliver an electrical signal, a drug, thermal energy, a cognitive task, or two or more thereof to one or more target tissues of the patient's body for treating a medical condition. For example, the controller 210 may receive manual instructions from an operator externally, or may cause an electrical signal to be generated and delivered based on internal calculations and programming. In other embodiments, the medical device 200 does not comprise a stimulation unit. In either embodiment, the controller 210 is capable of affecting substantially all functions of the medical device 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc.

The medical device 200 may also comprise a power supply 230. The power supply 230 may comprise a battery, voltage regulators, capacitors, etc., to provide power for the operation of the medical device 200, including delivering the therapeutic electrical signal. The power supply 230 comprises a power source that in some embodiments may be rechargeable. In other embodiments, a non-rechargeable power source may be used. The power supply 230 provides power for the operation of the medical device 200, including electronic operations and the electrical signal generation and delivery functions. The power supply 230 may comprise a lithium/thionyl chloride cell or a lithium/carbon monofluoride (LiCFx) cell if the medical device 200 is implantable, or may comprise conventional watch or 9V batteries for external (i.e., non-implantable) embodiments. Other battery types known in the art of medical devices may also be used.

The medical device 200 may also comprise a communication unit 260 capable of facilitating communications between the medical device 200 and various devices. In particular, the communication unit 260 is capable of providing transmission and reception of electronic signals to and from a monitoring unit 270, such as a handheld computer or PDA that can communicate with the medical device 200 wirelessly or by cable. The communication unit 260 may include hardware, software, firmware, or any combination thereof.

The medical device 200 may also comprise one or more sensor(s) 212 coupled via sensor lead(s) 211 to the medical device 200. The sensor(s) 212 are capable of receiving signals related to a physiological parameter, such as the patient's heart beat, blood pressure, and/or temperature, and delivering the signals to the medical device 200. The sensor 212 may also be capable of detecting kinetic signal associated with a patient's motor activity. The sensor 212, in one embodiment, may be an accelerometer. The sensor 212, in another embodiment, may be an inclinometer. In another embodiment, the sensor 212 may be an actigraph. The sensor(s) 212 may be implanted, or in other embodiments, the sensor(s) 212 are external structures that may be placed on the patient's skin, such as over the patient's heart or elsewhere on the patient's torso, limbs or head. The sensor 212, in one embodiment is a multimodal signal sensor capable of detecting various autonomic and neurologic signals, including kinetic/motor signals, metabolic signals, endocrine signals, stress markers signals associated with the patient's seizures.

In one embodiment, the medical device 200 may comprise a body data collection module 275 that is capable of collecting body data, e.g., cardiac data comprising fiducial time markers of each of a plurality of heart beats or arterial or venous pulsations; brain electrical or chemical signals; kinetic signals indicative of the patient's motor activity and/or cognitive functions (e.g., complex reaction time responses, memory, language); endocrine signals; body stress marker signals; body integrity/physical fitness signals; etc. More information about such signals and their detection can be found in U.S. patent application Ser. Nos. 12/896,525; 13/098,262; and Ser. No. 13/288,886; which are hereby incorporated by reference in their entirety.

The body data collection module 275 may also process or condition the body signal data. The body signal data may be provided by the sensor(s) 212. The body data collection module 275 may be capable of performing any necessary or suitable amplifying, filtering, and performing analog-to-digital (A/D) conversions to prepare the signals for downstream processing. The body data collection module 265, in one embodiment, may comprise software module(s) that are capable of performing various interface functions, filtering functions, etc. In another embodiment, the body data collection module 275 may comprise hardware circuitry that is capable of performing these functions. In yet another embodiment, the body data collection module 275 may comprise hardware, firmware, software and/or any combination thereof.

The body data collection module 275 is capable of collecting body data and providing the collected body data to a seizure onset/termination unit 280.

The seizure onset/termination unit 280 is capable of detecting an onset and/or a termination of an epileptic event based upon at least one body signal provided by body data collection module 275. The seizure onset/termination unit 280 can implement one or more algorithms using the autonomic data and neurologic data in any particular order, weighting, etc. The seizure onset/termination unit 280 may comprise software module(s) that are capable of performing various interface functions, filtering functions, etc. In another embodiment, the seizure onset/termination unit 280 may comprise hardware circuitry that is capable of performing these functions. In yet another embodiment, the seizure onset/termination unit 280 may comprise hardware, firmware, software and/or any combination thereof.

In addition to components of the medical device 200 described above, a medical device system may comprise a storage unit to store an indication of at least one of seizure or an increased risk of a seizure. The storage unit may be the memory 217 of the medical device 200, another storage unit of the medical device 200, or an external database, such as a local database unit 255 or a remote database unit 250. The medical device 200 may communicate the indication via the communications unit 260. Alternatively or in addition to an external database, the medical device 200 may be adapted to communicate the indication to at least one of a patient, a caregiver, or a healthcare provider.

In various embodiments, one or more of the units or modules described above may be located in a monitoring unit 270 or a remote device 292, with communications between that unit or module and a unit or module located in the medical device 200 taking place via communication unit 260 via a communication connection 297. For example, in one embodiment, one or more of the body data collection module 275 or the seizure onset/termination unit 280 may be external to the medical device 200, e.g., in a monitoring unit 270. Locating one or more of the body data collection module 275 or the seizure onset/termination unit 280 outside the medical device 200 may be advantageous if the calculation(s) is/are computationally intensive, in order to reduce energy expenditure and heat generation in the medical device 200 or to expedite calculation.

The monitoring unit 270 may be a device that is capable of transmitting and receiving data to and from the medical device 200. In one embodiment, the monitoring unit 270 is a computer system capable of executing a data-acquisition program. The monitoring unit 270 may be controlled by a healthcare provider, such as a physician, at a base station in, for example, a doctor's office. In alternative embodiments, the monitoring unit 270 may be controlled by a patient in a system providing less interactive communication with the medical device 200 than another monitoring unit 270 controlled by a healthcare provider. Whether controlled by the patient or by a healthcare provider, the monitoring unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, a cellular telephone, etc. The monitoring unit 270 may download various parameters and program software into the medical device 200 for programming the operation of the medical device, and may also receive and upload various status conditions and other data from the medical device 200. Communications between the monitoring unit 270 and the communication unit 260 in the medical device 200 may occur via a wireless or other type of communication, represented generally by line 277 in FIG. 2. This may occur using, e.g., a wand to communicate by RF energy with an implantable signal generator 110. Alternatively, the wand may be omitted in some systems, e.g., systems in which the MD 200 is non-implantable, or implantable systems in which monitoring unit 270 and MD 200 operate in the MICS bandwidths.

In one embodiment, the monitoring unit 270 may comprise a local database unit 255. Optionally or alternatively, the monitoring unit 270 may also be coupled to a database unit 250, which may be separate from monitoring unit 270 (e.g., a centralized database wirelessly linked to a handheld monitoring unit 270). The database unit 250 and/or the local database unit 255 are capable of storing various patient data. These data may comprise patient parameter data acquired from a patient's body, therapy parameter data, seizure severity data, and/or therapeutic efficacy data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions (e.g., programming detection parameters for a responsive therapy and/or setting references for one or more detection parameters) using the monitoring unit 270, which may include obtaining and/or analyzing data from the medical device 200 and/or data from the database unit 250 and/or the local database unit 255. The database unit 250 and/or the local database unit 255 may store various patient data.

One or more of the blocks illustrated in the block diagram of the medical device 200 in FIG. 2 may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units associated with the various blocks illustrated in FIG. 2 may be combined into a programmable device, such as a field programmable gate array, an ASIC device, etc.

Figure 3:
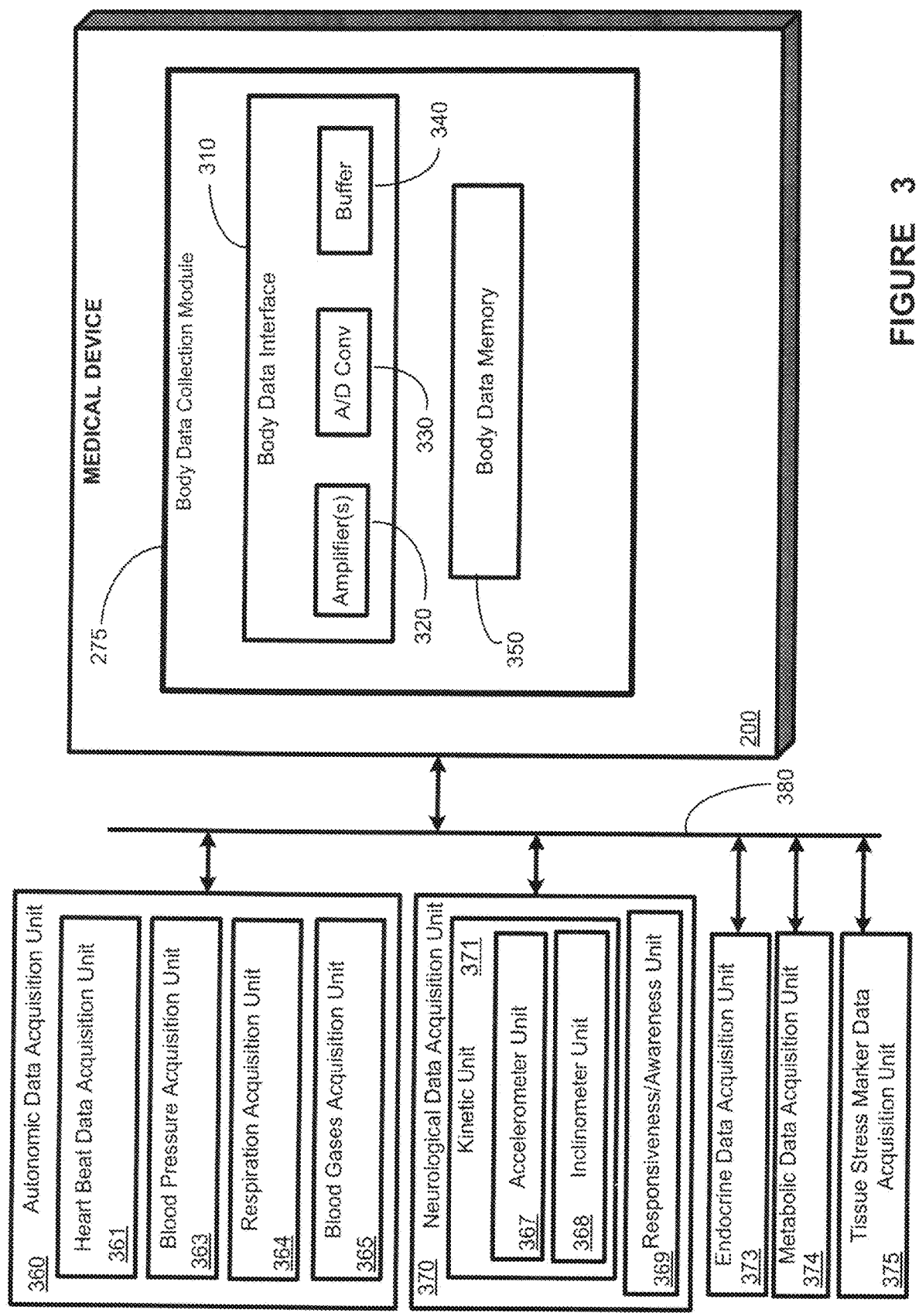
FIG. 3 provides a schematic representation of a number of data acquisition units of a medical device system, in accordance with one aspect of the present disclosure.

Turning now to FIG. 3, a block diagram depiction of an exemplary implementation of the body data collection module 275 is shown. The body data collection module 275 may include a body data memory 350 (which may be independent of memory 117 or part of it) for storing and/or buffering data. The body data memory 350 may be adapted to store body data for logging or reporting and/or for future body data processing and/or statistical analyses. Body data collection module 275 may also include one or more body data interfaces 310 for input/output (I/O) communications between the body data collection module 275 and sensors 112.

In the embodiments of FIG. 3, sensors 112 may be provided as any of various body data units/modules (e.g., autonomic data acquisition unit 360, neurological data acquisition unit 370, endocrine data acquisition unit 373, metabolic data acquisition unit 374, tissue stress marker data acquisition unit 375, and physical fitness/integrity determination unit via connection 380. Connection 380 may be a wired connection, a wireless connection, or a combination of the two. Connection 380 may be a bus-like implementation or may include an individual connection (not shown) for all or some of the body data units.

In one embodiment, the autonomic data acquisition unit 360 may include a cardiac data acquisition unit 361 adapted to acquire a phonocardiogram (PKG), EKG, echocardiography, apexcardiography and/or the like, a blood pressure acquisition unit 363, a respiration acquisition unit 364, a blood gases acquisition unit 365, and/or the like. In one embodiment, the neurologic data acquisition unit 370 may contain a kinetic unit 371 that may comprise an accelerometer unit 367, an inclinometer unit 368, and/or the like; the neurologic data acquisition unit 370 may also contain a responsiveness/awareness unit 369 that may be used to determine a patient's responsiveness to testing/stimuli and/or a patient's awareness of their surroundings. Other units (not shown) that may be used to acquire body data include, but are not limited to, tools for chemical assays, optical measuring tools, pressure measuring tools, and temperature measuring tools. Body data collection module 275 may collect additional data not listed herein, that would become apparent to one of skill in the art having the benefit of this disclosure.

The body data acquisition units ([360-370], [373-377]) may be adapted to collect, acquire, receive/transmit heart beat data, EKG, PKG, echocardiogram, apexcardiogram, blood pressure, respirations, blood gases, body acceleration data, body inclination data, EEG/ECoG, quality of life data, physical fitness data, and/or the like.

The body data interface(s) 310 may include various amplifier(s) 320, one or more A/D converters 330 and/or one or more buffers 340 or other memory (not shown). In one embodiment, the amplifier(s) 320 may be adapted to boost and condition incoming and/or outgoing signal strengths for signals such as those to/from any of the body data acquisition units/modules (e.g., ([360-370], [373-377])) or signals to/from other units/modules of the MD 200. The A/D converter(s) 330 may be adapted to convert analog input signals from the body data unit(s)/module(s) into a digital signal format for processing by controller 210 (and/or processor 215). A converted signal may also be stored in a buffer(s) 340, a body data memory 350, or some other memory internal to the MD 200 (e.g., memory 117, FIG. 1) or external to the MD 200 (e.g., monitoring unit 170, local database unit 155, database unit 150, and remote device 192). The buffer(s) 340 may be adapted to buffer and/or store signals received or transmitted by the body data collection module 275.

As an illustrative example, in one embodiment, data related to a patient's respiration may be acquired by respiration unit 364 and sent to MD 200. The body data collection module 275 may receive the respiration data using body data interface(s) 310. As the data is received by the body data interface(s) 310, it may be amplified/conditioned by amplifier(s) 320 and then converted by A/D converter(s) into a digital form. The digital signal may be buffered by a buffer(s) 340 before the data signal is transmitted to other components of the body data collection module 275 (e.g., body data memory 350) or other components of the MD 200 (e.g., controller 110, processor 115, memory 117, communication unit 160, or the like). Body data in analog form may be also used in one or more embodiments.

Body data collection module 275 may use body data from memory 350 and/or interface 310 to calculate one or more body indices. A wide variety of body indices may be determined, including a variety of autonomic indices such as heart rate, blood pressure, respiration rate, blood oxygen saturation, neurological indices such as maximum acceleration, patient position (e.g., standing or sitting), and other indices derived from body data acquisition units 360, 370, 373, 374, 375, 376, 377, etc.

Figure 4:
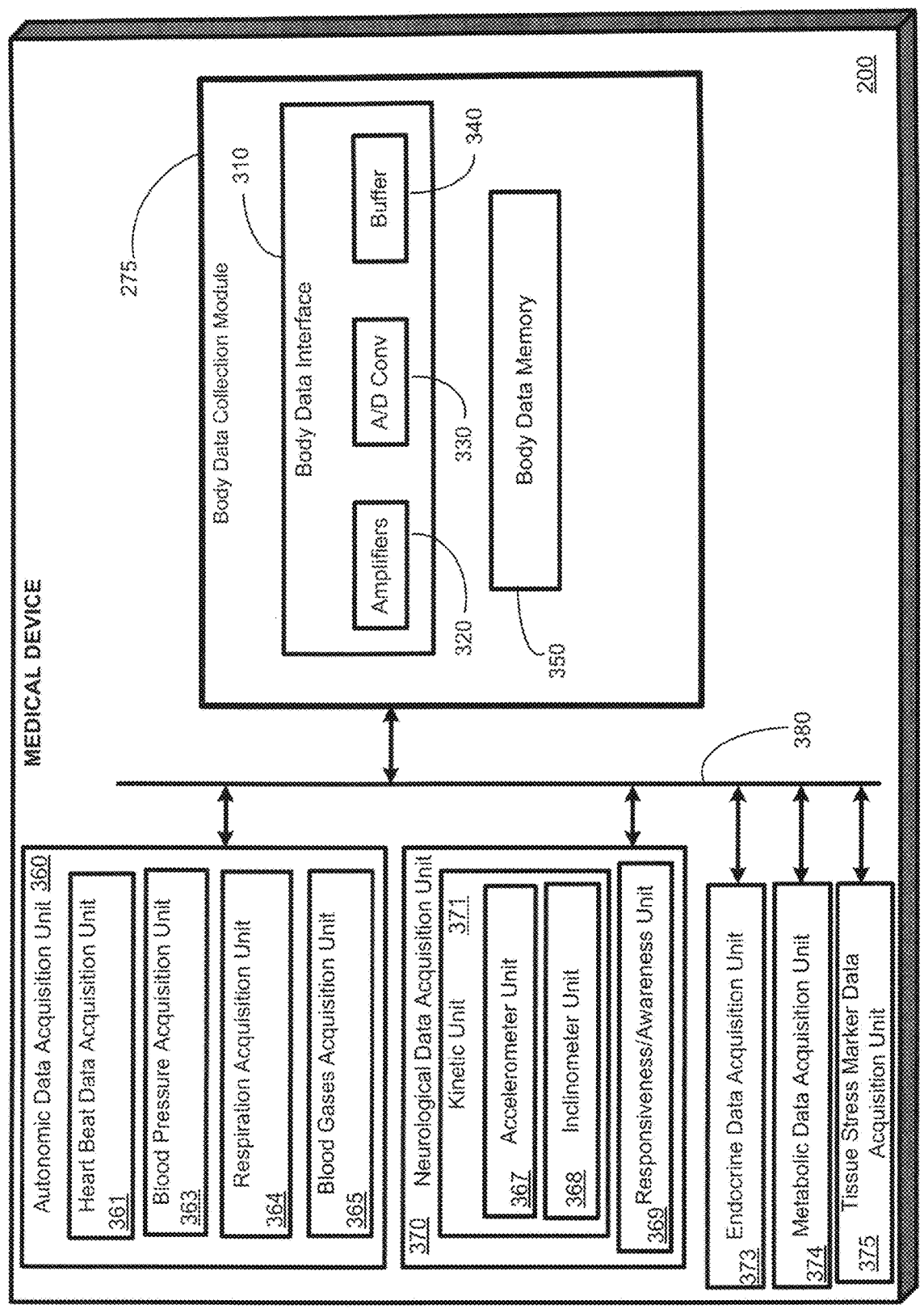
FIG. 4 provides a schematic representation of a number of data acquisition units of a medical device system, in accordance with one aspect of the present disclosure.

Turning now to FIG. 4, an MD 200 (as described in FIG. 3) is provided, in accordance with one illustrative embodiment of the present invention. FIG. 4 depicts the body data acquisition units similar to those shown in FIG. 3, in accordance with another embodiment, wherein these units are included within the MD 200, rather being externally coupled to the MD 200, as shown in FIG. 3. In accordance with various embodiments, any number and type of body data acquisition units may be included within the MD 200, as shown in FIG. 4, while other body data units may be externally coupled, as shown in FIG. 3. The body data acquisition units may be coupled to the body data collection module 275 in a fashion similar to that described above with respect to FIG. 3, or in any number of different manners used in coupling intra-medical device modules and units The manner by which the body data acquisition units may be coupled to the body data collection module 275 is not essential to, and does not limit, embodiments of the instant invention as would be understood by one of skill in the art having the benefit of this disclosure. Embodiments of the MD depicted in FIG. 4 may be fully implantable or may be adapted to be provided in a system that is external to the patient's body.

A time series body signal collected by the body data collection module 275 may comprise at least one of a measurement of the patient's heart rate, a measurement of the patient's kinetic activity, a measurement of the patient's brain electrical activity, a measurement of the patient's oxygen consumption, a measurement of the patient's work, a measurement of an endocrine activity of the patient, a measurement of a metabolic activity of the patient, a measurement of an autonomic activity of the patient, a measurement of a cognitive activity of the patient, or a measurement of a tissue stress marker of the patient.

Figure 5:
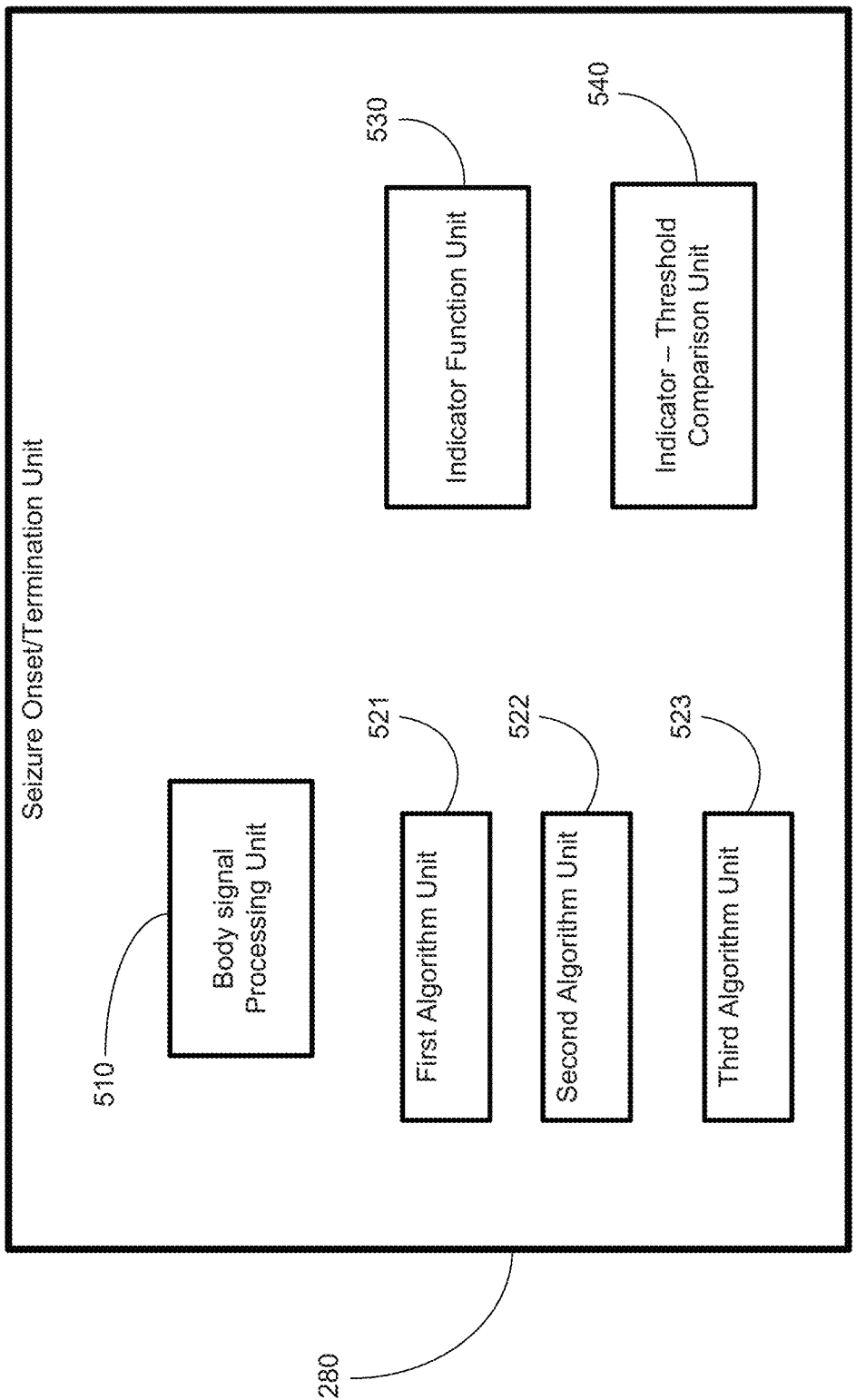
FIG. 5 provides a schematic representation of a seizure onset/termination unit of a medical device system, in accordance with one aspect of the present disclosure.
Figures 6A, 6B:
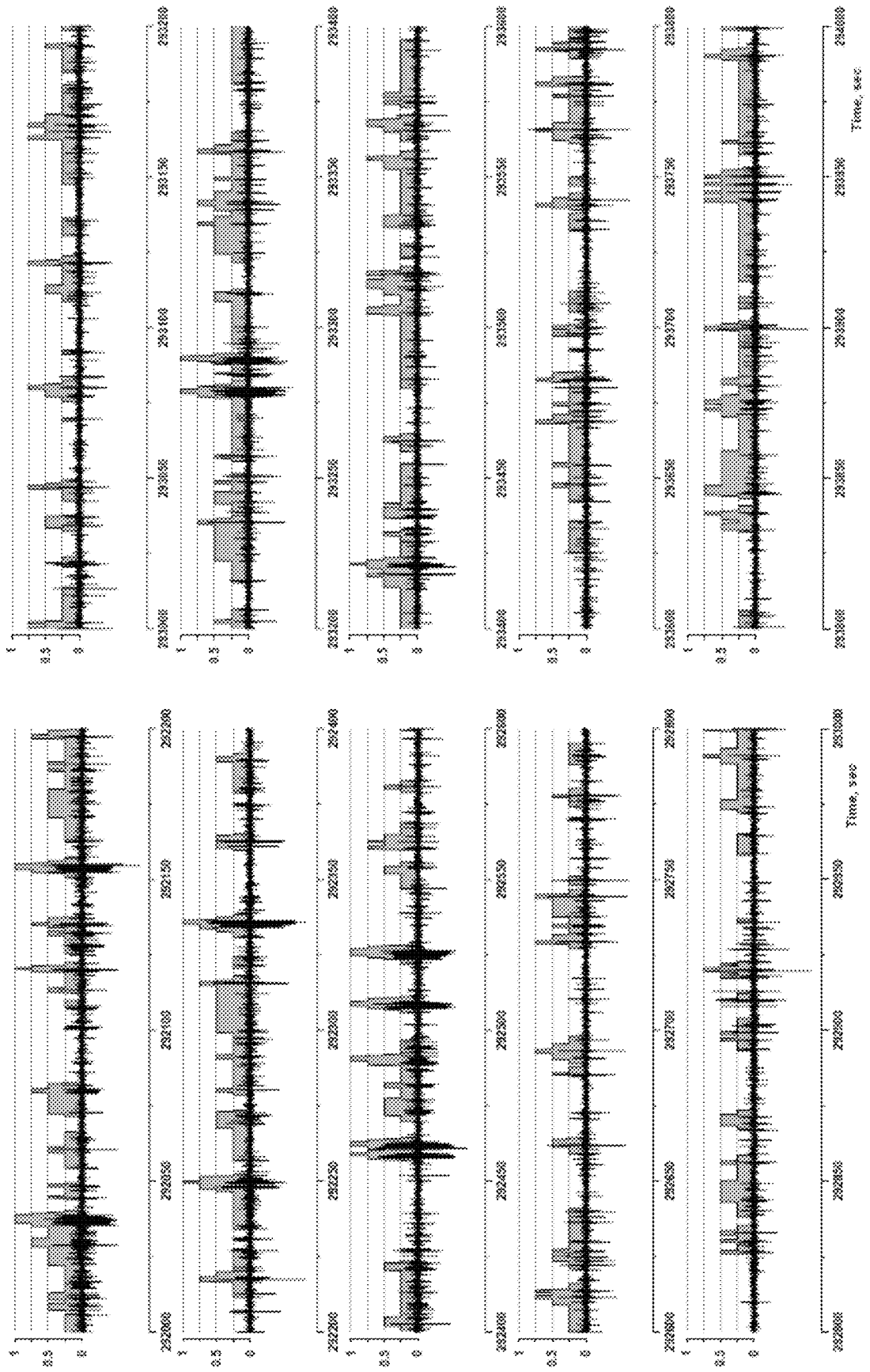
FIG. 6a-d. Average Indicator Function value (AIF; grey step-wise functions) of the probability that cortical activity (black oscillations) is a seizure over a certain time interval.
Figures 6C, 6D:
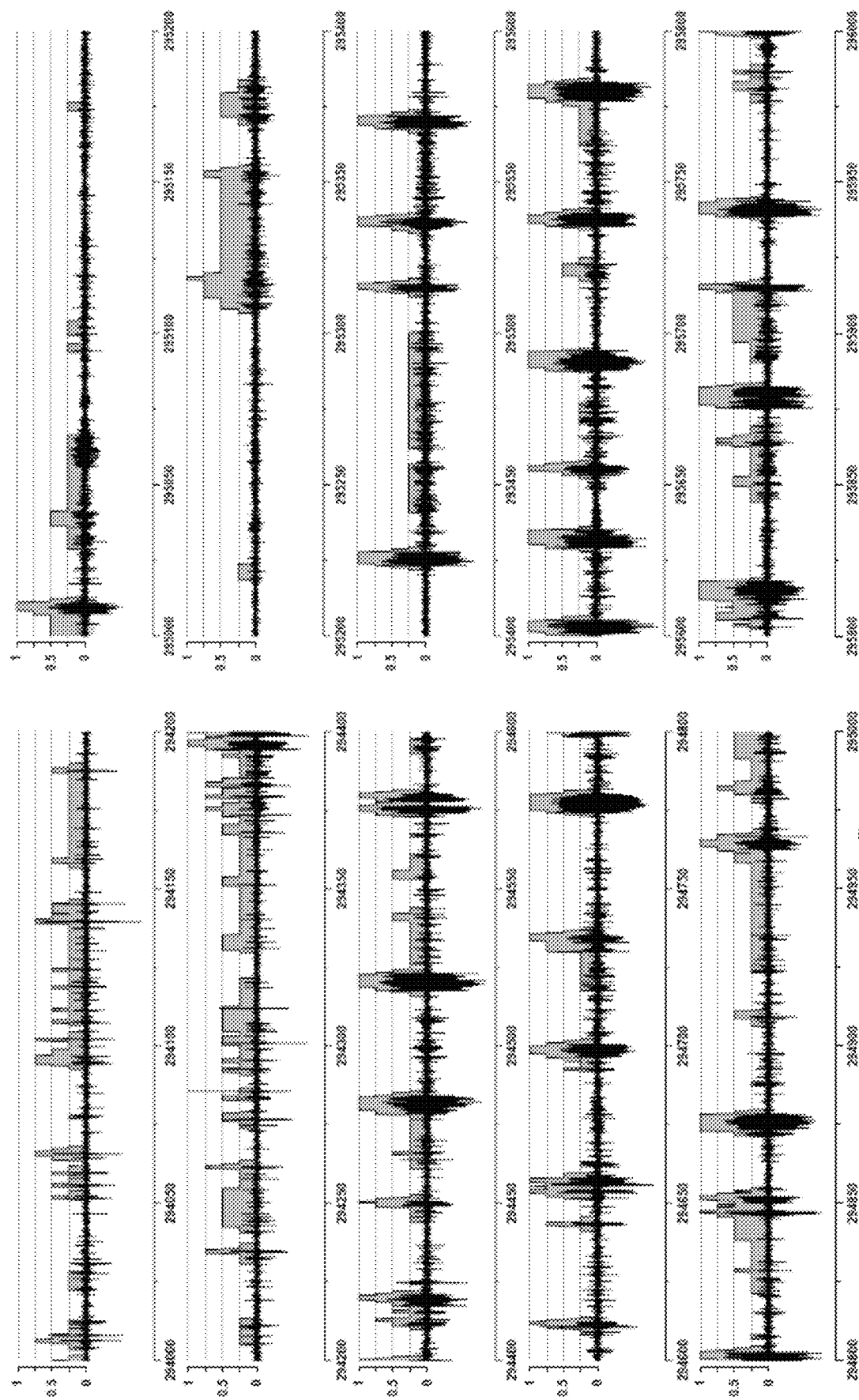

Turning to FIG. 5, the seizure onset/termination unit 280 depicted in FIG. 2 is shown in greater detail. The seizure onset/termination unit 280 may comprise a body signal processing unit 510 adapted to process collected body data from the body data collection module 275. For example, the seizure onset/termination unit 280 may be adapted to receive a time series of collected body data.

The seizure onset/termination unit 280 may also comprise a plurality of algorithm units 521, 522, 523, and optionally others not shown. Each algorithm unit 521, etc. may apply an algorithm to body signal data to determine an occurrence of a seizure, as described herein. At least two algorithms may be applied to at least one body signal. In one embodiment, detection algorithms operating in real-time may be used, and in another embodiment, real-time and/or off-line algorithms (not operating in real-time due to window length or computational demands) may be used to confirm in a probabilistic way detections made in real-time. The PMSA may thus be applied to body signal time series in: 1. Real-time/on-line for detection, therapy delivery, and warning purposes, and 2. Off-line for assessment of algorithm/PMSA performance and/or tracking of disease status (e.g., progression or regression) through quantification of event frequency, severity, inter-event intervals, or time spent in seizure, etc. More detail on tracking disease status and the like can be found in U.S. patent application Ser. Nos. 12/816,348 and 12/816,357, both filed Jun. 15, 2010, and both hereby incorporated herein by reference.

Body signals may belong to the same class (e.g., cardiac) or to different classes (e.g., cardiac, neurologic, endocrine) and each signal class has subclasses; for example, cardiac signals may be electrical (EKG), acoustic (PKG, Echocardiography), or thermal, and neurological signals may be chemical or optical, among others. Real-time and/or off-line analyses may be performed on at least one biological signal class (e.g., cardiac) or on to at least two (e.g., cardiac, neurologic and metabolic). Furthermore, within each class one or more sub-classes may be analyzed with at least one algorithm; in the case of cardiac signals, EKG, PKG, and pulse pressure may be chosen for event detection and in that of neurological signals, the analyzed subclasses may be ECoG, responsiveness/awareness or kinetic. The number of possible signal analyses permutations of detection algorithms, signal classes and signal subclasses for estimation of a PMSA is $n_{algorithms} \times n_{classes} \times n_{sub-classes}$.

Multiple average indicator functions (AIFs) may be derived for computing a PMSA:

$AIF_{uni-class}(t) = 1/N \, \Sigma \, X_{algorithms(1 \ldots n)}(t)$
$AIF_{uni-class/multi-subclass}(t) = 1/N \, \Sigma \, X_{algorithms(1 \ldots n)}(t)$
$AIF_{multi-class/uni-sub-class}(t) = 1/N \, \Sigma \, X_{algorithms(1 \ldots n)}(t)$
$AIF_{multi-class-multi-subclass(1 \ldots n)}(t) = 1/N \, \Sigma \, X_{algorithms(1 \ldots n)}(t)$ Similarly, multiple product indicator functions may be derived for computing a PMSA:

$PIF_{uni-class}(t) = X_{algorithm1}(t) \cdot X_{algorithm2}(t) \cdot X_{algorithm3}(t) \cdot X_{algorithmn}(t)$
$PIF_{uni-class/multi-subclass}(t) = X_{algorithm1}(t) \cdot X_{algorithm2}(t) \cdot X_{algorithm3}(t) \cdot \cdot X_{algorithmn}(t)$
$PIF_{multi-class/uni-sub-class}(t) = X_{algorithm1}(t) \cdot X_{algorithm2}(t) \cdot X_{algorithm3}(t) \cdot \cdot X_{algorithmn}(t)$
$PIF_{multi-class-multi-subclass}(t) = X_{algorithm1}(t) \cdot X_{algorithm2}(t) \cdot X_{algorithm3}(t) \cdot \cdot X_{algorithmn}(t)$ The seizure onset/termination unit 280 may also comprise an indicator function (IF) unit 530. The IF unit 530 may be adapted to determine an indicator function, such as an average indicator function (AIF), or a product indicator function (PIF) to the outputs of algorithm units 521, etc., which may be weighted linearly or non-linearly. In the case of the PIF, weights are meaningfully applied only when the all the indicator functions have a value of 1.

The seizure onset/termination unit 280 may also comprise an indicator-threshold comparison unit 540. The indicator-threshold comparison unit 540 may be adapted to compare a value of an IF output by the IF unit 530 to a detection threshold value.

A medical device or medical device system as shown in one or more of FIGS. 2-5 may be configured to perform in whole or in part one or more methods described below.

As shown in FIG. 15, in one aspect, the present disclosure provides a method of detecting a seizure in a patient.

The method may comprise providing at 1510 at least first and second seizure detection algorithms for detecting seizure activity based upon at least one body signal or at least one class of body signals.

The at least first and second seizure detection algorithms may be selected from an autoregression algorithm, a wavelet transform maximum modulus (WTMM) algorithm, or a short-term-average to long-term-average (STALTA) algorithm, such as those described above. Any other algorithms may be applied to a time series to generate indicator functions to compute an AIF or a PIF.

The at least one body signal may comprise at least one of a measurement of the patient's autonomic, neurologic, endocrine, or metabolic activity, or a measurement of a tissue stress marker of the patient. In various exemplary embodiments, a measurement of an autonomic activity may be a measurement of at least one of a cardiac signal, a respiratory signal a measurement of the patient's oxygen consumption, a measurement of the patient's oxygen saturation, a measurement of a skin signal or of catecholamines; a measurement of neurologic signal may be at least one of a measurement of a cognitive signal, a measurement of a kinetic signal, or a measurement of a brain electrical or chemical signal; a measurement of a metabolic signal may be at least one of a measurement of an arterial pH, a measurement of an electrolyte signal, or a measurement of a glucose signal; a measurement of an endocrine signal may be at least one of a measurement of a prolactin signal and a measurement of a cortisol signal, a measurement of a body stress marker signal may be at least one of a measurement of a lactic acid signal and a measurement of a prostane signal. Pressure measurements in brain, heart, or vascular tree may be also performed.

The method may also comprise determining at 1520 a probabilistic measure of seizure activity (PMSA) based upon the outputs of the at least first and second seizure detection algorithms. In one embodiment, determining at 1520 may comprise determining an average indicator function by averaging the outputs of the at least first and second seizure detection algorithms. In another embodiment, determining at 1520 may comprise determining a product indicator function by multiplying the outputs of the at least first and second seizure detection algorithms. In yet another embodiment, determining at 1520 may comprise determining both the average and product indicator functions, without weights, or linearly or non-linearly weighted.

In one optional aspect, the method may further comprise selecting one or more of a number of seizure detection algorithms (i.e., whether one, two, three, four, or a greater number of seizure detection algorithms are to be used), the at least first and second seizure detection algorithms (i.e., which particular seizure detection algorithms are to be used), at least one parameter of at least one of the first and second seizure detection algorithms, a type of the PMSA (e.g., a PIF, an AIF, or another type of PMSA), or at least one parameter of the PMSA (e.g., a weighting between IFs making up the PMSA; a threshold for the PMSA value) based upon one or more of: a clinical application; a level of safety risk associated with an activity; at least one of an age, physical state, or mental state of the patient; a length of a window available for warning; a degree of efficacy of therapy and of the latency of its effect; a degree of seizure control; a degree of circadian and ultradian fluctuations of the patient's seizure activity; a performance of the detection method as a function of the patient's sleep/wake cycle or vigilance level; a dependence of the patient's seizure occurrence on at least one of a level of consciousness, a dependence of the patient's seizure occurrence on circadian or ultradian rhythms, a level of cognitive activity, or a level of physical activity; the site of seizure origin; a seizure type or class; a proclivity for the seizure to spread or to impair cognitive or motor functions; a proclivity of the seizure to cause falls to the ground; a time elapsed from a previous seizure; a desired sensitivity of detection of a seizure; a desired specificity of detection of a seizure: a desired speed of detection of a seizure; a time elapsed since a previous seizure; a previous seizure severity; a probability of seizure occurrence; a likelihood of seizure occurrence; an input provided by a person (e.g., the patient or a care-giver); or an input provided by a machine/device (e.g., a sensor).

In one embodiment, the number of algorithms, the specific algorithms, the parameters of the PMSA (e.g., the weighting, the threshold), etc. may be established based at least in part on at least one of a measurement of the patient's heart activity, a measurement of the patient's respiratory activity, a measurement of the patient's kinetic activity, a measurement of the patient's brain electrical activity, a measurement of the patient's oxygen consumption, a measurement of the patient's oxygen saturation, a measurement of an endocrine activity of the patient, a measurement of a metabolic activity of the patient, a measurement of an autonomic activity of the patient, a measurement of a cognitive activity of the patient, or a measurement of a tissue stress marker of the patient. In certain embodiments, such a basis may be a form of adaptation since the signal values may be different for each signal class and for each subclass. For example, a kinetic signal may be the first one to change in certain seizures (e.g., convulsions), while a heart rate signal may be the last one to increase (e.g., in partial seizures originating outside central autonomic brain regions; said increase manifesting only when it becomes generalized).

The choice of multiple parameters, e.g., a body signal and PMSA threshold value, may be performed independently of one another based on their positive predictive value and/or information content. For example, a person of ordinary skill in the art may choose a body signal that gives high sensitivity and/or specificity for seizure detection, and also choose the PMSA threshold based on the clinical application, time of day, etc. For example, when the patient is in bed, the PMSA threshold may be set higher than when the patient is standing, when kinetic body signals indicative of convulsions are used by the algorithm(s).

In various embodiments, the selected parameters may reflect the degree of certainty of detections desired by the patient, a caregiver, a medical professional, or two or more thereof. Such person(s) are expected to have biases regarding their desire for certainty of detection, and variations or differences in their risk-proneness and/or aversion to risk. Thus, in one embodiment, the patient, caregiver, and/or medical professional may be allowed to change (within certain limits and for certain activities only, if desired) the sensitivity, specificity, and/or speed of detection of the algorithms.

Parameters of the PMSA include, but are not limited to, the AIF or PIF value at which a seizure onset and/or termination is declared, or the weights assigned to the various algorithms used in calculating an AIF or PIF. Thus, in one aspect, the method may comprise comparing the PMSA to a PMSA threshold value, and detecting at 1530 a seizure event when the PMSA reaches or exceeds the PMSA threshold, imposing, when desirable, duration constraints. In one embodiment, wherein n algorithms are used in an AIF without weighting, the PMSA threshold may be (n−1)÷n. For example, if four algorithms are used in an AIF, without weights, then the PMSA threshold may be 0.75, indicating three of the four algorithms agree a seizure event has occurred or is occurring. In a further embodiment, the method may additionally comprise adaptively setting the PMSA threshold value. For example, the threshold value may be adaptively set based on one or more of time of day or risk of seizure, among other considerations. The adaption may be performed manually (e.g., by the patient or a caregiver) or automatically (e.g., by a controller 210 operating on data stored in memory 217, monitoring unit 270, database unit 250, etc. and suitably programmed to adapt the threshold).

Upon a determination at 1520 of the PMSA, one or more optional actions may be performed. For example, the method may further comprise delivering at 1540 a therapy for the seizure at a particular time, wherein at least one of the therapy, the particular time, or both is based upon the PMSA value. In a further embodiment, the method may further comprise determining at 1550 at least one of an efficacy of the therapy or an occurrence of at least one side effect of the therapy. For another example, the method may further comprise issuing at 1560 a warning for the seizure, wherein the warning is based upon the PMSA value, the type of warning being commensurate with said value. For another example, the method may further comprise logging at 1570 one or more values relating to the seizure severity (e.g., a duration of the seizure; an intensity of the seizure; a degree of spread of the seizure in the brain of the patient; or a fraction of time spent in the seizure over a moving time window), the detection and termination times and date, the type of therapy and its length, efficacy and the side effects if any, the warning type and duration, or other information of interest to the person of ordinary skill in the art, as well as information about the physical integrity of the patient.

In one embodiment, at least one of the delivered therapy or the issued warning may be based at least in part on the type of activity engaged in by the patient at the time of seizure onset, the seizure type, the seizure severity, or the time elapsed from the last seizure.

Turning to FIG. 16, a method of detecting a seizure in accordance with one embodiment of the present disclosure is depicted. In the depicted embodiment, a first body signal may be received at 1610 by a first sensor and a second body signal by a second sensor. Exemplary body signals are set forth above. The first and second sensors may both be sensors of one type (e.g., two electrodes configured to receive brain electrical signals), wherein the at least two sensors are sited at separate locations on or in a patient's body, or may be of multiple types (e.g., electrical, chemical, optical, pressure sensors) configured to detect a patient's body signals located on or in a patient's body. The first and second body signals may be of the same class or subclass, or may be of different classes. In one particular embodiment, the first and second body signals may be from two different subclasses from at least one signal class.

From a signal, a PMSA may then be determined at 1620. In other words, seizure detections each based on a data stream received by one of the at least two sensors can be used in a PMSA, comparably to the way multiple algorithms operating on the same data stream were used in a PMSA in embodiments discussed above. That is, in view of the number of combinations of $n_{algorithms} \times n_{classes} \times n_{sub\text{-}classes}$ making up a PMSA, in one embodiment, $n_{algorithms}$ may be 1 and the total of ($n_{classes} + n_{subclasses}$) may be 2 or more. In other embodiments, of course, $n_{algorithms}$ may be 2 or more and the total of ($n_{classes} + n_{subclasses}$) may be 1 or more.

In one embodiment, only one sensor placed on the organ or site of interest and a reference one may be used.

Turning to FIG. 17, a method of detecting a seizure in a patient is depicted. The method of FIG. 17 contains numerous elements in common with FIG. 15. Those elements have been described above and need not be described further.

In the method of FIG. 17, a wavelet transform maximum modulus-stepwise approximation (WTMM-Sp) algorithm for detecting seizure activity based upon at least one body signal may be provided at 1710. As described earlier, a WTMM-Sp algorithm can be used to generate a plurality of outputs indicative of detection of a seizure. The method may thus comprise determining at 1520 a probabilistic measure of seizure activity (PMSA) based upon a plurality of outputs of the WTMM-Sp algorithm.

Figure 18:
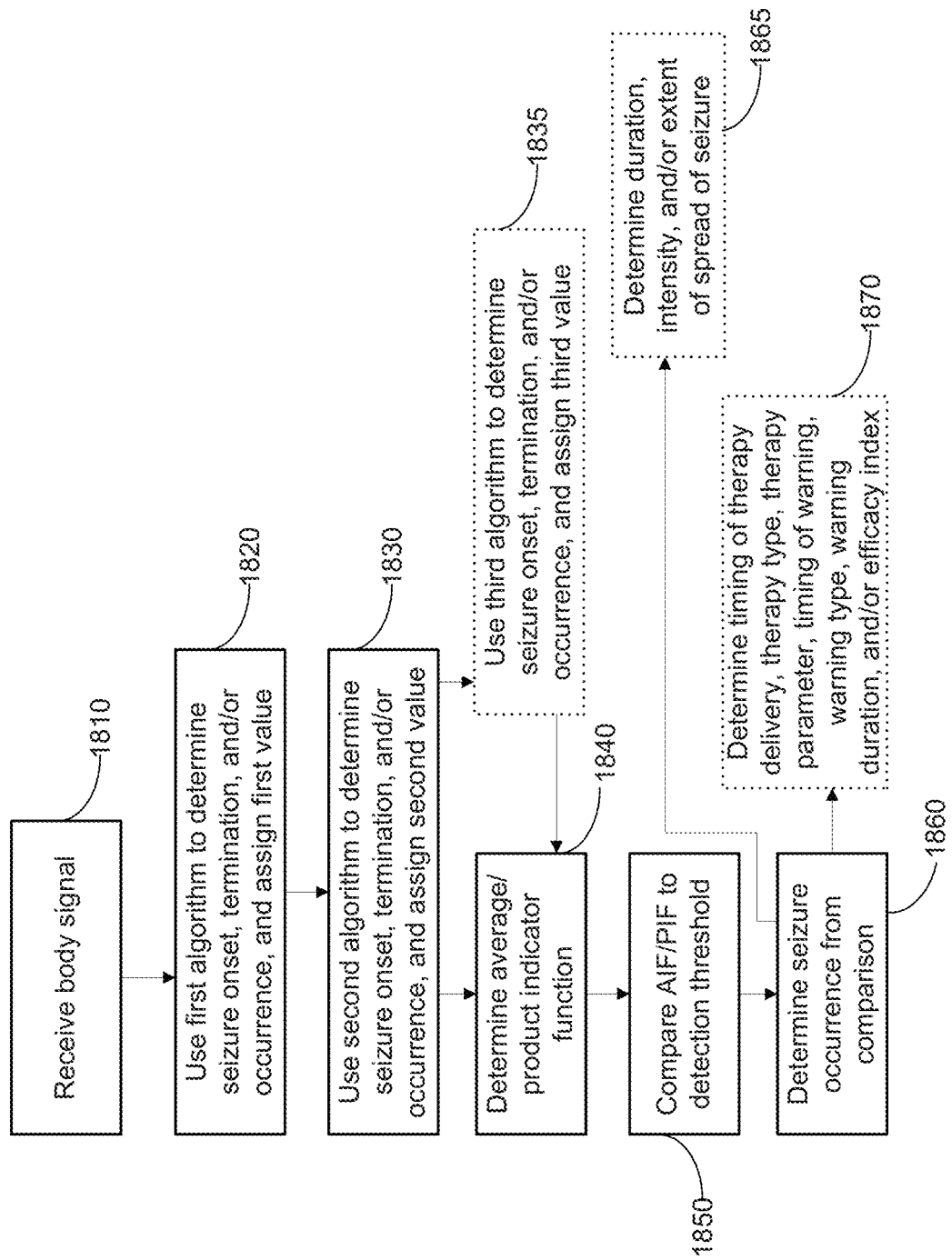
FIG. 18 provides a flowchart depiction of a method, in accordance with one aspect of the present disclosure.

Turning to FIG. 18, another method in accordance with one illustrative embodiment of the present disclosure is depicted.

The method may comprise receiving at 1810 at least one body signal. Exemplary body signals have been described herein.

The method may comprise using at 1820 a first algorithm to determine at least one of a seizure onset, seizure termination, or an occurrence of a seizure from the at least one body signal, and to assign a first value based upon a determination that at least one of the seizure onset, seizure termination, or the occurrence of a seizure has occurred. The first algorithm may be an autoregression algorithm, a WTMM algorithm, or a STA/LTA algorithm, as described herein.

The method may comprise using at 1830 a second algorithm to determine at least one of the seizure onset, seizure termination, or the occurrence of a seizure from the at least one body signal, and to assign a second value based upon a determination that at least one of the seizure onset, seizure termination, or an occurrence of a seizure has occurred. The second algorithm may be an autoregression algorithm, a WTMM algorithm, or a STA/LTA algorithm, as described herein.

Optionally, the method may further comprise using at 1835 a third algorithm to determine at least one of the seizure onset, seizure termination, or the occurrence of a seizure from the at least one body signal, and to assign a third value based upon a determination that at least one of the seizure onset, seizure termination, or the occurrence of a seizure has occurred. The third algorithm may be an autoregression algorithm, a WTMM algorithm, or a STA/LTA algorithm, as described herein.

Additional algorithms may be used to assign additional values, if desired.

Based on the assigned values, the method may comprise determining at 1840 an average indicator function (AIF) value or a product indicator function (PIF) value. AIFs and PIFs have been described herein.

The method may comprise comparing at 1850 the AIF value or the PIF value to a detection threshold, said threshold being fixed, adaptable, or self-adaptive.

The method may comprise determining at 1860 that a seizure has occurred based upon a determination that the AIF value is above the threshold or PIF value equals one. For example, if an AIF is determined at 1840, the AIF threshold value may be to be e.g. 0.66 (thus resulting in a determination at 1860 by agreement between 2/3, or a greater fraction of algorithms) or 0.75 (thus resulting in a determination at 1860 by agreement between 3/4 or a greater fraction of algorithms).

Optionally, the method may further comprise other actions. In one embodiment, the method may further comprise determining at 1865 at least one of the duration, the intensity, or the extent of spread of the seizure.

Alternatively or in addition, the method may further comprise determining at 1870 at least one of a timing of delivery of therapy, a rate of delivery of a therapy, a therapy type, a timing of sending a warning, a warning type, a warning duration, or an efficacy index based upon a timing of the average indicator function value.

A non-transitory computer readable program storage unit encoded with instructions that, when executed by a computer, may perform any method described herein.

In one or more of the methods described above, an activity, such as walking, swimming, driving, etc., may be allowed, precluded, or terminated, a warning may be issued or not issued, or a therapy may be delivered or not delivered, based on the PMSA value.

At least one algorithm may be selected based on at least one of specificity, sensitivity, positive predictive value (PPV), or speed of detection.

PMSA may be used to determine, in whole or in part, at least one of a probability of delivering a warning, a probability of delivering a therapy, a type of a warning, a type of a treatment, or a site or sites of delivery of a treatment.

PMSA may be weighted by latency to at least one of loss of responsiveness, seizure severity (SS), seizure frequency (SF), time between seizures (TBS), or efficacy of a therapy. This weighting may allow adapting a probabilistic seizure detection to the patient's seizure type, frequency, and/or severity.

The signals analyzed by the algorithms used in determining the PMSA may be collected simultaneously or substantially simultaneously (to yield what may be termed an "instantaneous PSMA") or may be collected over a non-simultaneous period of time (to yield what may be termed as a "staggered PMSA").

The algorithm(s) selected for use in determining the PSMA may be ranked in hierarchy based on one or more of speed of detection, specificity, sensitivity, or other parameters.

An "efficacy index" (which may be termed "EI") may be used herein to refer to any quantification of an efficacious result of a therapy. In one example, if a patient typically presents with an increase in heart rate from a resting rate of 80 beats per minute (BPM) to a peak ictal heart rate of 160 BPM, and upon administering a therapy to the patient, the patient's peak ictal heart rate is 110 BPM, this result may be quantified as an efficacy index in a number of ways. For example, an efficacy index may be calculated as (nontherapy peak ictal heart rate) minus (peak ictal heart rate after therapy), e.g., in this example, 50. For another example, an efficacy index may be calculated as (reduction from peak ictal heart rate brought about by therapy) divided by (increase from resting rate to peak ictal heart rate in the absence of therapy), e.g., in this example, 50/80, or 0.625. Other ways of calculating an efficacy index may be used.

A probabilistic efficacy index (PEI) may also be computed. In some embodiments, the probabilistic efficacy index may be given by the difference in the value of the PMSA of un-treated compared to that of treated seizures (PMSA$_{un-treated}$-PMSA$_{treated}$), or by the differences of PMSA value between a first and a second therapy (PMSA$_{therapy1}$-PMSA$_{therapy2}$). For example, if a PMSA value calculated using an AIF based on four algorithms is 1 (meaning all algorithms are in agreement) 60 sec. after issuance of a detection in untreated seizures, and 0.25 (meaning only one of the four algorithms identifies a seizure) two seconds after termination of a 1 sec. therapy, triggered 2 sec. after detection (e.g., at 5 sec after issuance of a detection in the treated seizure), the PEI may be calculated as the difference in PMSA values (in this example, 1−0.25=0.75) multiplied by the difference in time after detection at which the PMSA values are calculated (in this example, 60 sec−5 sec=55 sec). In other words, in this example, the PEI is 0.75×55 (sec)=42. The PEI of this example, or one calculated in a similar manner, may be considered a time-based PEI. In another embodiment, the PEI may be independent of time and reflect only the PMSA differences between un-treated and treated seizures. For example, a time-independent PEI from the foregoing example may be calculated as the difference in PMSA values (e.g., 1−0.25=0.75).

Further, the efficacy index EI may be added to or multiplied by the PEI to generate a comprehensive efficacy index CEI. CEI=EI+PEI or CEI=EI×PEI.

Whether or not to use PIF or AIF may be based on at least one of a clinical application of the output; a level of safety risk associated with an activity; an age, physical and mental state of the patient; a history of degree of concordance or discordance of outputs of seizure detection algorithms applied to the signal; a length of a window available for warning before the patient becomes impaired; a degree of efficacy of therapy and of the latency of its effect; a degree of seizure control; or a degree of circadian and ultradian fluctuations of PMSA and of its dependence on a level of consciousness, a level of cognitive activity and a level of physical activity. The number of algorithms and particular algorithms used in the PIF or AIF may each be based on at least one of a clinical application of the output; a level of safety risk associated with an activity; an age, physical and mental state of the patient; a history of degree of concordance or discordance of outputs of seizure detection algorithms applied to the signal; a length of a window available for warning; a degree of efficacy of therapy and of its latency; a degree of seizure control; or a degree of circadian and ultradian fluctuations of PMSA and of its dependence on a level of consciousness, a level of cognitive activity and a level of physical activity.

PIF may have a faster computation than AIF. Mathematically, if one of the inputs to a PIF is zero, the PIF must be zero. Therefore, a calculation of a PIF can be stopped when the first zero is encountered among the inputs to the function.

All of the methods and apparatuses disclosed and claimed herein may be made and executed without undue experimentation in light of the present disclosure. While the methods and apparatus of this disclosure have been described in terms of particular embodiments, it will be apparent to those skilled in the art that variations may be applied to the methods and apparatus and in the steps, or in the sequence of steps, of the method described herein without departing from the concept, spirit, and scope of the disclosure, as defined by the appended claims. It should be especially apparent that the principles of the disclosure may be applied to selected cranial nerves other than, or in addition to, the vagus nerve to achieve particular results in treating patients having epilepsy, depression, or other medical conditions.

The particular embodiments disclosed above are illustrative only as the disclosure may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the disclosure. Accordingly, the protection sought herein is as set forth in the claims below.

The invention claimed is:

1. A method, comprising:
   determining via one or more processors of one or more medical devices, by a first seizure detection algorithm and a second seizure detection algorithm for detecting seizure activity based upon at least one body signal, at least a first output of seizure detection of the first seizure detection algorithm, wherein the first output is zero when the first seizure detection algorithm detects no seizure and the first output is one when the first seizure detection algorithm detects a seizure, and a second output of seizure detection of the second seizure detection algorithm, wherein the second output is zero when the second seizure detection algorithm detects no seizure and the second output is one when the second seizure detection algorithm detects the seizure;
   determining via the one or more processors of the one or more medical devices a probabilistic measure of seizure activity (PMSA) value based upon at least the first output and the second output of the first seizure detection algorithm and the second seizure detection algorithm, wherein the determining the PMSA value comprises determining an average indicator function based on the first output and the second output of the first seizure detection algorithm and the second seizure detection algorithm;
   comparing the PMSA value to a PMSA threshold, and detecting a seizure event when the PMSA value meets or exceeds the PMSA threshold; and
   delivering a therapy based on the probabilistic measure of seizure activity value meeting or exceeding the PMSA threshold, where the therapy is a delivery of at least one of an electrical signal, a drug, and a thermal energy to one or more target tissues of a patient's body;
   wherein the first seizure detection algorithm and the second seizure detection algorithm are one of: an autoregression algorithm; a wavelet transform maximum modulus (WTMM) algorithm; and a short-term-average to long-term-average (STA/LTA) algorithm;
   wherein the at least one body signal comprises at least one of a measurement of the patient's heart activity, a measurement of the patient's respiratory activity, a measurement of the patient's kinetic activity, a measurement of the patient's brain electrical activity, a measurement of the patient's brain chemical activity, a measurement of the patient's brain temperature, a measurement of the patient's oxygen consumption, a measurement of the patient's oxygen saturation, a measurement of an endocrine activity of the patient, a measurement of a metabolic activity of the patient, a measurement of an autonomic activity of the patient, a measurement of a cognitive activity of the patient, and a measurement of a tissue stress marker of the patient.

2. The method of claim 1, further comprising:
   selecting one or more of the autoregression algorithm, the wavelet transform maximum modulus (WTMM) algorithm, and the short-term-average to long-term-average (STA/LTA) algorithm, the first seizure detection algorithm and the second seizure detection algorithm, at least one parameter of at least one of the first seizure detection algorithm and the second seizure detection algorithm, a type of the PMSA, and at least one parameter of the PMSA, based upon one or more of:
   a clinical application; a level of safety risk associated with an activity; at least one of an age, a physical state, and a mental state of the patient; a length of a window available for a warning; a degree of efficacy of the therapy and a therapy latency effect; a degree of seizure control; a degree of circadian and ultradian fluctuations of the patient's seizure activity; a performance of a detection method as a function of the patient's sleep/wake cycle or vigilance level; a dependence of the patient's seizure detection on at least one of a level of consciousness, a circadian or ultradian rhythm, a level of cognitive activity, or a level of physical activity; a site of seizure origin; a seizure type or class; a proclivity for the seizure to spread or to impair cognitive or motor functions; a proclivity of the seizure to cause falls to a ground; a desired sensitivity of detection of the seizure; a desired specificity of detection of the seizure: a desired speed of detection of the seizure; a time elapsed since a previous seizure; a previous seizure severity; a probability of seizure occurrence, a probability of seizure detection; a likelihood of seizure detection; and an input provided by a user or by a machine.

3. The method of claim 2, wherein the selecting is one of a manual selection or an automatic adaptive selection.

4. The method of claim 1, wherein the PMSA threshold is established based at least in part on at least one of a measurement of the patient's heart activity, a measurement of the patient's respiratory activity, a measurement of the patient's kinetic activity, a measurement of the patient's brain electrical activity, a measurement of the patient's oxygen consumption, a measurement of the patient's oxygen saturation, a measurement of an endocrine activity of the patient, a measurement of a metabolic activity of the patient, a measurement of an autonomic activity of the patient, a measurement of a cognitive activity of the patient, or a measurement of a tissue stress marker of the patient.

5. The method of claim 1, wherein the PMSA threshold is established based at least in part on at least one of a level of safety risk associated with an activity; at least one of an age, physical state, or mental state of the patient; a length of a window available for warning; a degree of efficacy of the therapy and of a therapy's latency; a degree of seizure control; a degree of circadian and ultradian fluctuations of the patient's seizure activity; a performance of the detection method as a function of the patient's sleep/wake cycle or vigilance level; a dependence of the patient's seizure activity on at least one of a level of consciousness, a level of cognitive activity, or a level of physical activity; the site of seizure origin; a seizure type; a desired sensitivity of detection of a seizure; a desired specificity of detection of a seizure: a desired speed of detection of a seizure; an input provided by a user; an input provided by a machine; a time elapsed since a previous seizure; a previous seizure severity; a probability of seizure detection or a likelihood of seizure detection.

6. The method of claim 1, wherein the first seizure detection algorithm and the second seizure detection algorithm operate in real-time or off-line.

* * * * *